United States Patent [19]

Cone, Jr.

[11] Patent Number: 4,724,234

[45] Date of Patent: Feb. 9, 1988

[54] METHOD FOR PRODUCING ONCOLYSIS

[75] Inventor: Clarence D. Cone, Jr., Yorktown, Va.

[73] Assignee: Therapeutical Systems Corp., Yorktown, Va.

[21] Appl. No.: 792,257

[22] Filed: Oct. 28, 1985

Related U.S. Application Data

[63] Continuation of Ser. No. 419,324, Sep. 17, 1982, abandoned.

[51] Int. Cl.$^4$ .................. A61K 31/045; A61K 31/20; A61K 31/195
[52] U.S. Cl. .................................. 514/728; 514/558; 514/561
[58] Field of Search ................ 514/580, 728, 558, 561

[56] References Cited

PUBLICATIONS

Chem. Abst. 73: 12786g, 1970; 73: 18358h, 1970; 69: 65737g, 1968; 70: 1785g, 1969.

Haskell, Cancer Treatment, Saunders Co., Philadelphia, 2nd ed. 1985, Chapter 76, pp. 889–896.

*Primary Examiner*—J. R. Brown
*Assistant Examiner*—John W. Rollins, Jr.

[57] ABSTRACT

A method of producing oncolysis and regression of malignant tumors and other malignant conditions without adverse effects on normal body cells is described. A calorically and compositionally defined nutritional regimen providing a minimum of amino acids and fatty acids and a maximum of carbohydrates is administered concurrently with a drug regimen of an agent or agents that uncouple oxidative phosphorylation, most preferably 2,4-dinitrophenol.

30 Claims, 5 Drawing Figures

METHOD FOR PRODUCING ONCOLYSIS

This application is a continuation of application Ser. No. 419,324 filed Sept. 17, 1982, now abandoned.

Reference is made to Disclosure Document No. 096829 filed by the present inventor on Jan. 9, 1981 which relates to the present invention. Permanent retention thereof is hereby requested.

BACKGROUND OF THE INVENTION

When the adenosine triphosphate (ATP) pool in a cell is depleted below the level which must be maintained to meet the cellular needs for maintenance of metabolic processes, the cell is not only incapable of mitotic division but the cell dies. The rate of change in the ATP pool size existing in a cell at any particular time is the difference between the rate at which ATP is being produced, primarily by oxidative phosphorylation along the respiratory chain (RC) in the mitochondria, and the rate at which ATP is being used up (hydrolyzed) to provide substantially all the energy requirements of the cell. This energy is principally required for all the myriad anabolic and catabolic reactions in the metabolism of the cell, and for powering the "sodium pumps" of the pericellular membrane—whose collective action keeps the intracellular $Na^+$-concentration relatively low despite the continuous leakage of $Na^+$ through the membrane into the cell from the high $Na^+$-concentration extracellular fluid. The fundamental pathway involved in ATP production and usage (hydrolysis) in all normal body cells is depicted in FIG. 1.

The abbreviations used in FIG. 1 and elsewhere throughout this application are explained in the following table:

TABLE

| | |
|---|---|
| AA | amino acids |
| AcCoA | acetyl coenzyme A |
| ADP | adenosine diphosphate |
| Amr | active metabolic rate |
| ATP | adenosine triphosphate, the basic compound for storing chemical energy in the cell |
| ATPase | adenosine triphosphatase |
| Bmr | basal metabolic rate (expressed as a multiple of pretreatment Bmr or Mayo Normal Standard Bmr) |
| Ca | calcium |
| CAC | Citric Acid Cycle |
| Cho | carbohydrate component of Dnr |
| $Cl^-$ | ion |
| d | day |
| DNP | 2,4-dinitrophenol |
| Dnr | defined nutritional regimen |
| Efa | essential fatty acid component of Dnr |
| EMP | Embden-Meyerhof Pathway |
| $Emr_A$ | effective (average) metabolic rate |
| FA | fatty acids |
| g | gram |
| I | iodine |
| Kcal | kilocalories |
| kg | kilogram |
| $lO_2/d$ | liters of $O_2$ consumed metabolically, per day (24 hours) |
| Mg | magnesium |
| mg | milligram |
| ml | milliliter |
| Mn | manganese |
| $Na^+$ | sodium ion |
| NADH | reduced nicotinamide adenine dinucleotide |
| $O_2$ | molecular oxygen |
| O/P | oxidative phosphorylation |
| P | phosphorus |
| Pr | protein component of Dnr |

TABLE-continued

| | |
|---|---|
| Pr = 15 | denotes protein allowance basis for Dnr-protein; 15 g protein per 70 kg body weight |
| $Pr_{min}$ | minimum protein allowance to maintain nitrogen equilibrium |
| RC | respiratory chain |
| Se | selenium |
| SP | sodium pump |
| UA | uncoupling agent |
| V + M | vitamins + minerals mix (daily amount supplied) |
| $W_B$ | body weight (kg) |
| Zn | zinc |

In normal (i.e., nonmalignant) body cells, the key nutritional component from which the fundamental energy supply for synthesizing ATP is derived is glucose. Glucose is transformed by the sequential reactions of the Glycolytic or Embden-Meyerhof Pathway (EMP) into pyruvate. Subsequently, pyruvate is decarboxylated and forms acetyl coenzyme A (AcCoA) which then enters the citric acid cycle (CAC) in the mitochondria. Here each acetate moiety, after first being incorporated into a molecule of citric acid, is broken down into $CO_2$ and H with the H appearing, inter alia, in molecules of reduced nicotinamide adenine dinucleotide (NADH) which then contain a large fraction of the energy contained in the original glucose. This NADH subsequently is oxidized in the mitochondrial respiratory chain (RC) with the ultimate production of $H_2O$ by terminal reaction of the H with molecular $O_2$; this $O_2$ is readily supplied by the normal vasculature. The energy obtained by the transport of electrons down the potential gradient of the RC, by a sequence of redox reactions, is used to produce the ATP of the cell. Thus, in normal cells, the ATP-stored energy is obtained in the major proportion from nutritional glucose or from carbohydrates (i.e., starches and sugars) yielding glucose upon digestion. Some ATP-energy is obtained in normal cells from the oxidation, in the citric acid cycle, of fatty acids and amino acids obtained from nutritional fats and proteins. When adequate glucose is available in the nutriment intake, however, all major ATP-energy needs of normal cells are readily obtainable from glucose alone. The ATP produced in the respiratory chain enters the cellular "ATP Pool", from which it is continuously withdrawn to supply the energy needs of total cellular metabolism and to power the membrane sodium pumps which keep the intracellular $Na^+$-concentration adequately low by the outpumping of $Na^+$.

This same general pattern of ATP generation and usage obtains in malignant cells, but with two crucial differences. First, it has been extensively demonstrated that malignant cells in general possess a distinctive metabolic aberrancy, ostensibly as an innate consequence of their transformation to the malignant state. Under in vivo conditions, malignant cells in tumors do not substantially convert pyruvate to AcCoA (see FIG. 2); the pyruvate instead is essentially converted to lactate and is excreted from the cell. [Busch, H., *An Introduction to the Biochemistry of the Cancer Cell* Chapter 10, Academic Press, New York (1962)]. The net consequence is that only a very small fraction of the chemical energy in glucose can be extracted and used by the cancer cell, compared to that available to the normal cell. Since nutritional glucose is by far the most prominent and important source of normal cellular ATP energy under normal conditions, this transformation aberrancy puts the malignant cell at a great disadvantage regarding the maximal rates at which it can generate ATP. This metabolic defect is particularly detrimental for the malignant cell, which generally needs an especially abundant supply rate of ATP to support the highly active metabolism associated with the frequent mitosis characteristic of these highly proliferative cells.

However, the malignant cell quite effectively circumvents this deficiency under usual nutritional conditions by ready oxidation of fatty acids and amino acids in the citric acid cycle. Mitochondria possess a very efficient enzyme system capable of effecting the "$\beta$-oxidization" of fatty acids directly to AcCoA, which then enters the citric acid cycle and is oxidized exactly as the AcCoA produced from glucose is oxidized in normal cells. The amino acids are similarly reduced to AcCoA or other intermediates of the CAC and then oxidized, after initial deamination. Thus, some amino acid species are capable of entering the citric acid cycle directly at various intermediate points of the cycle, after deamination and suitable transformation, all readily accomplished by the enzyme systems of the malignant cell. Consequently, although substantially deprived of the utilization of glucose as a primary energy source, the malignant cell makes full use of the supply of the energy-rich fatty acids, and amino acids, all present in the plasma under usual nutritional intake level. In anorexic patients having low food intake in the very late stages of malignancy, the profound cachexia observed attests to the effectiveness with which fat and protein (muscle) depots have been mobilized, and thus fatty acids and amino acids made available to the malignant cells for their continued proliferation, while the patient becomes emaciated.

In accordance with the present invention, the ATP pool of malignant cells in the body is depleted to a level which is inadequate for maintenance of the essential metabolic processes of these cells, without substantially altering the normal ATP pool size in the normal cells of the body.

The present therapy consists of two parts, administered concurrently. The first part of the therapy is designed to severely limit the maximum rate at which the cancer cells can potentially produce ATP via the respiratory chain (RC), without limiting to any significant extent the rate at which normal cells can potentially produce ATP. The second part is designed to grossly reduce the actual net ATP production rate of the cancer cells by uncoupling a major part of their oxidative phosphorylation, without altering the actual ATP production rate of the normal cells from their normal level. The pronounced net deficit in the ATP production rate, relative to that necessary just to supply the minimal ATP rate requirements of the essential metabolic processes, soon reduces the ATP pool size selectively in the cancer cells to a subminimal level inadequate for continued vital functioning. Degeneration, lysis, or functional death of the cancer cells then ensues.

The first part of the therapy system comprises the administration of a defined nutritional regimen (Dnr) which consists essentially of a nutritional regimen designed to maximize the use of nutritional carbohydrates as a source of ATP energy, and to minimize the use of nutritional fatty acids and amino acids for the same purpose.

The second part comprises a concurrently administered dosage of an agent effective to uncouple oxidative phosphorylation (UA) so as to greatly reduce the net ATP production rate of the cancer cells by uncoupling a large fraction of the maximum potential ATP production per unit time, a maximum already severely limited by the reduced availability of NADH resulting from the restriction of available fatty acids and amino acids by the Dnr. Since the normal cells can make full use of the abundant carbohydrate (glucose) supplied by the Dnr for energy purposes, the only effect on the normal cells is an increase in $O_2$ consumption rate; the potential ATP loss in the normal cells due to the uncoupling action is fully compensated by a higher rate of NADH oxidation by the respiratory chain, while the rate of actual net ATP production remains unchanged at its usual, normal level.

This invention encompasses the novel use, as effective anticancer agents in vivo in humans, of physiologically tolerable agents which uncouple oxidative phosphorylation. Applicant has demonstrated that the classical uncoupler 2,4-dinitrophenol (DNP), when used with the nutritional regimen of this invention, will bring about a rapid and marked reduction of size in a variety of malignant tumor types in humans. Such size reduction is characteristic clinical evidence for malignant cell lysis and degeneration, also termed oncolysis. Applicant's test results and other available information indicate that a like reduction in malignant cell content of tissues containing disperse or otherwise nonaggregated malignant cells will result from treatment in accordance with this invention.

Applicant has disclosed a related nutritional regimen as part of a different system for the treatment of cancer in U.S. patent application Ser. No 223,850, filed Jan. 9, 1981, but did not disclose the use of DNP or of other physiologically tolerable uncoupling agents as anticancer agents.

Physiologically tolerable agents that uncouple the oxidative energy-releasing centers of the respiratory chain from the ATP-yielding phosphorylation of adenosine diphosphate in the mitochondria of cells have been investigated extensively over the past thirty-five years in the study of oxidative metabolism [Demers, L. M. et al. *Proc. Soc. Exper. Med.* 140, 724 (1972); Hemker, H. C. *Biochem. Biophys. Acta* 63, 46 (1962); Hemker, H. C. *Biochem. Biophys. Acta* 48, 221 (1961); Heytler, P. G. "Uncouplers of Oxidative Phosphorylation" in Erecinski et al (eds.) *Inhibitors of Mitochondrial Functions* Pergamon 1981, p. 203]. Indeed it was observations of the effects of such agents on cell respiration that led to the discovery of the fundamental process of oxidative phosphorylation [Hotchkiss, *Adv. Enzymol.* 4, 153 (1944)]. Because of the vital importance of aerobic metabolism as the major source of cellular ATP production, even physiologically tolerable agents capable of effecting a substantial degree of uncoupling of oxidative phosporylation are potentially very toxic in excessive dosage and must obviously be utilized with great care. The underlying basis of all toxic effects in normal cells due to excessive uncoupling of oxidative phosphorylation lies in the concomitant reduction of the cellular ATP production rate below that required to support the essential metabolic needs of the cell for normal functioning. Consequently, since the principal effect of uncoupling is an accelerated rate of oxidation of NADH by the RC with a commensurate elevation in the $O_2$ consumption rate, the relative level of uncoupling by an uncoupling agent (UA) can be directly monitored by measurement of the whole-body basal metabolic rate (Bmr), in terms of $lO_2/d$. Thus, safe UA dosage ranges can be simply and effectively determined by careful monitoring of the Bmr, in conjunction with careful monitoring of carbohydrate intake to insure it meets the total daily caloric needs ($Emr_A$) of the body.

In the first major medical use of an uncoupling agent, the use of DNP for reduction of obesity, the absolute need for monitoring the Bmr to insure the maintenance of a proper level of safety was pointed out by the original investigators [Tainter, M. L. et al. *J. Am. Med. Assoc.* 101, 1472 (1933); Tainter, M. L. et al. *J. Phramacol. Exp. Therap.* 48, 410 (1933)], who emphasized that the administration of DNP must be performed only under close medical supervision and monitoring. These and other clinical investigators conducted a preliminary investigation of the dosage-effects properties of DNP in a wide range of animals and humans, and demonstrated the essential nonexistence of any deleterious side effects of DNP when the Bmr was held at the desired clinical level by administration of the appropriate dosage level of DNP [Borley, W. E. et al. *Arch. Opth.* 18, 908 (1937); Borley, W. E. et al. *Am. J. Ophth.* 21, 1091 (1938); Cutting, W. C. et al *J.A.M.A.* 101, 193 (1933); Cutting, W. C. et al. *J. Clin. Investigation* 13, 547 (1934); Schulte, T. L. *J. Pharm. Exper. Biol. Med.* 419 (1937); Schulte, T. L. et al. *Proc. Soc. Exper. Ther.* 31, 1163 (1934); Tainter, M. L. *J. Pharm. Exper. Ther.* 49, 187 (1933); Tainter, M. L. *J. Pharm. Exper. Ther* 51, 143 (1934); Tainter, M. L. *Proc. Soc. Exper Biol Med.* 31, 1161 (1934); Tainter, M. L. *J.A.M.A.* 104, 1071 (1935); Tainter, M. L. *J. Pharm. Exper Ther.* 63,51 (1938); Tainter, M. L. et al. *J. Pharm. Exper. Ther.* 53, 58 (1935); Tainter, M. L. et al. *Arch. Ophth* 29, 30 (1938); Tainter, M. L. et al. *J. Pharm. Exper. Ther.* 55, 326 (1935); Tainter, M. L. et al. *Am. J. Pub. Health* 24, 1045 (1934); Tainter, M. L. et al. *Arch. Path.* 18, 881 (1934); Tainter, M. L. et al. *J.A.M.A.* 101, 1472 (1933); Tainter, M. L. et al. *J.A.M.A.* 102, 1147 (1934); Terada, B. et al. *J. Pharm. Exper. Ther.* 54, 454 (1935)].

Unfortunately, the early success in the clinical use of DNP for obesity reduction soon led to its wide and indiscriminate use by the public, without professional supervision, for weight reduction. A multitude of weight reduction nostrums containing unspecified concentrations of DNP appeared on the non-prescription market. Abuse and overdoses, some even for suicidal purposes, yielded a complete profile on human toxicity effects [Parascondola, J. L. *Molecular and Cellular Biochemistry* 5, 69 (1974)]. A chronic toxic effect possibly related to DNP observed among the population at large in individuals on uncontrolled and unsupervised weight reduction programs, was the formation of cataracts in a small number of cases. [Horner, D. W. *Arch. Opth.* 27, 1097 (1942)]. However, such cataract formation, at much higher incidence levels, is particularly common in a number of physiological conditions in which there is hypoglycemia or an inability to transport glucose into cells at an adequate rate (starvation, chronic hypoglycemia, and diabetes mellitus), and the observed cataracts may have been the result of weight-reduction-associated hypoglycemia rather than a direct effect of DNP itself. The therapy system of the present invention innately and effectively insures the maintenance of normal or higher blood glucose levels at all times. Cataract formation has not been observed in any of a wide range of animal species given DNP, even at high dosages [Horner, D. W. *supra*]. Hitch, J. M. et al., *J. Am. Med. Assn.* 106, 2130 (1936) suggests a relationship between DNP ingestion and dermatitis exfoliativa, but this seems more likely a coincidental parallelism due to some other factor than DNP.

Because of the potential dangers of overdosage in uncontrolled use, and indiscriminate labeling of the myriad weight-reduction preparations containing DNP, the drug was removed from the market by the FDA. in 1938 [Parascandola, J. supra], and in 1939 the state of California made it a felony to sell, dispense, administer, or prescribe DNP for human consumption [Horner, D. W. supra]. The intent of these laws was manifestly to prevent public misuse and overuse of DNP as a weight reducing agent.

DNP or related phenol-derivatives have been used as skin cosmetics or therapeutic compositions for treatment of skin irritations [U.S. Pat. No. 2,281,937; Japanese patents Nos. 46-9158 and 46-5837]. DNP and related phenols have also been suggested as active agents in insecticides [U.S. Pat. No. 2,166,121; 2,210,894; 2,210,929], and in rat control preparations (Italian Pat. No. 440144).

The effect of DNP on one form of animal tumor in vivo was briefly investigated in 1933, but without the associated nutritional regimen provided by the present invention [Emge, L. A. et al. *Proc. Soc. Exp. Biol. Med.* 31, 152 (1933)]. In Emge, sarcoma tumors in rats injected with DNP did not show any macroscopic changes in growth rate.

The present applicant found in a preliminary evaluative clinical trial with far-advanced human cancer patients having histologically-verified malignancies representing a wide range of cancer types (breast, colon, lung, prostate, larynx, lymphoma) that a significant rate and extent of reduction in tumor size occurred when DNP was administered in coordination with a calorically and compositionally defined nutritional regimen defined individually for each patient, according to the present invention. The team of professionally qualified biochemists and medical oncology specialists monitoring the patient status throughout this clinical evaluation reported an absence, throughout the treatment regimen, of any discernable toxic side effects.

The therapy system of the present invention substantially avoids several of the traditional problems and limitations of conventional mitoxin chemotherapy. Mitoxin chemotherapy characteristically acts by the indiscriminate destruction of mitotic cells in the body, both normal and malignant. Because of this indiscriminate destruction of normal dividing cells by mitoxin chemotherapy, a host of toxic and treatment-limiting side effects are experienced, including anemia, pronounced loss of cellular and humoral immune competence, decrease of blood platelets, gastrointestinal ulceration with vomiting and diarrhea, electrolyte imbalance, anorexia, loss of hair, abnormalities of the nervous system, kidney damage, skin rash, liver damage, abnormal heart beat, and damage to the lungs. The present method of metabolic chemotherapy, because it does not adversely affect normal dividing cells in the body, is strikingly free of all such toxic effects and therefore permits continued administration until potentially all of the malignant cells are destroyed.

Similarly, since the present method does not destroy blastogenic lymphocytes of the immune system as does mitoxin chemotherapy, the body's immune competence remains unaltered, thus avoiding the pronounced decrease in resistance to infectious disease usually seen in human patients undergoing chemotherapy, and maximally enhancing potential immunological cell-mediated and humoral attack on residual tumor cells.

Furthermore, the present invention substantially avoids the traditional mitoxin-chemotherapy problem of resistant malignant-cell variants arising by mutation during the course of cancer therapy. The uncoupling effects produced by DNP and other physiologically tolerable uncoupling agents of similar function do not generally depend upon the reaction with a specific functional protein (e.g., an enzyme) or upon the chemical structure of the uncoupling agent [See Heytler, P. G. "Uncouplers of Oxidative Phosphorylation" in Erecinski et al. (eds.) *Inhibitors of Mitochondrial Functions* Pergamon 1981, p. 203], unlike the situation in the case of the often-mutagenic mitoxin chemotherapeutical agents. Hence, it is unlikely that populations of cancer-cell mutants resistant to uncoupling agents will arise (e.g., by one-step mutations) in the course of treatment with the present method.

Additionally, since the present method does not require a cancer cell to be in the proliferative or dividing cycle in order to effect its lysis, the present method is fully and continuously effective against even those generally present clones of mitotically quiescent malignant cells which are entirely unaffected by the conventional mitoxin chemotherapeutical drug and therefore survive to produce continual tumor recurrences following the conventional mitoxin chemotherapeutical treatments.

A most significant advantage of the present method is the pronounced increase in O/P uncoupling effectiveness produced selectively in the cancer cells relative to that produced in normal cells by the same dosage of uncoupling agent, particularly by the most preferred (2,4-dinitrophenol) and preferred uncoupling agents of this invention. Since the uncoupling effectiveness of the classical O/P uncoupling agents [Heytler, P. G., 1981, supra]depends upon their lipid solubility [Hemker, H. C. supra], and since the lipid solubility increases very rapidly as the intracellular pH is lowered (i.e., acidity is increased) [Hemker, H. C. ibid], the relatively very low pH of the cancer cells resulting from the very high rate of lactate formation under the therapeutical conditions results in a pronounced selective increase in O/P uncoupling, and a commensurate decrease in net ATP production rate, in the cancer cells. Thus, for a given dosage level of UA, the uncoupling produced in the cancer cells may be selectively magnified up to several times that produced in the normal cells.

BRIEF DESCRIPTION OF THE INVENTION

The present invention affords a novel method of substantially reducing or eliminating a wide variety of malignancies in humans and other mammals. The effect on the malignancy is oncolysis; that is, lysis, degeneration or death of the malignant cells. Specifically, the novel method encompasses the concurrent administration by skilled professionals of two therapeutic regimens. One regimen is a defined nutritional regimen (Dnr) individually designed for each patient to minimize the use of amino acids and fatty acids as an energy source for ATP synthesis within the cell, with the result that cancer cells, which use amino acids and fatty acids to the substantial exclusion of carbohydrates, are selectively starved for energy sources. The daily Dnr caloric level is calculated from measurements of the daily whole-body $O_2$ consumption. The second regimen is the administration of a physiologically tolerable agent, e.g. 2,4-dinitrophenol (DNP) in an individually-tailored amount sufficient to uncouple oxidative phosphorylation, so that a major part of such ATP as would otherwise have been generated in the cancer cells in a particular patient under the Dnr regimen per unit time is wasted through uncoupling.

The efficacy of the method of this invention and the absence of toxic side effects have been demonstrated in a clinical setting with terminally-ill human cancer patients. Patients with tumors representing a wide variety of malignancy types all responded to the therapy of the present invention. The method has great promise for effectively treating many malignancies that are substantially untreatable by present day methods.

DETAILED DESCRIPTION OF THE INVENTION

Figure 4:
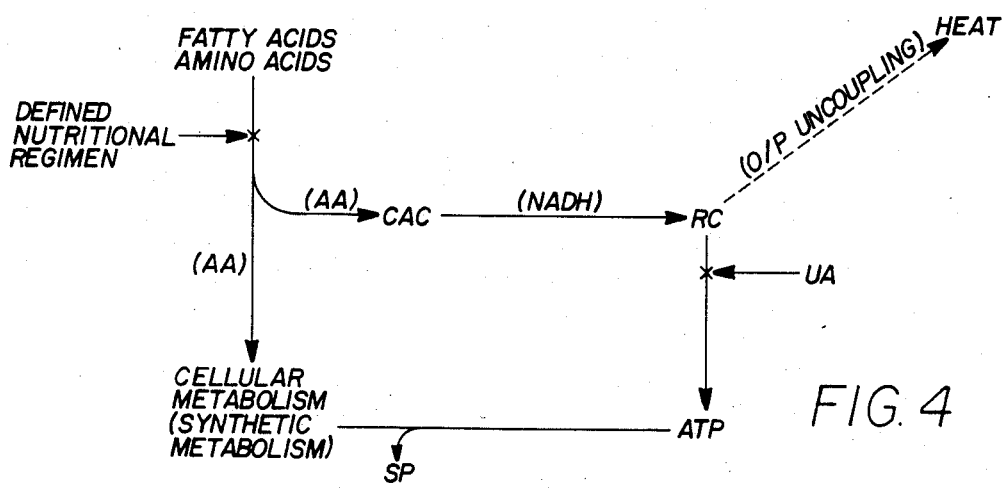
FIG. 4 is a flow diagram depicting the regulatory pathways of amino acid metabolism in malignant cells subjected to the Dnr and UA treatment of this invention.
Figure 3:
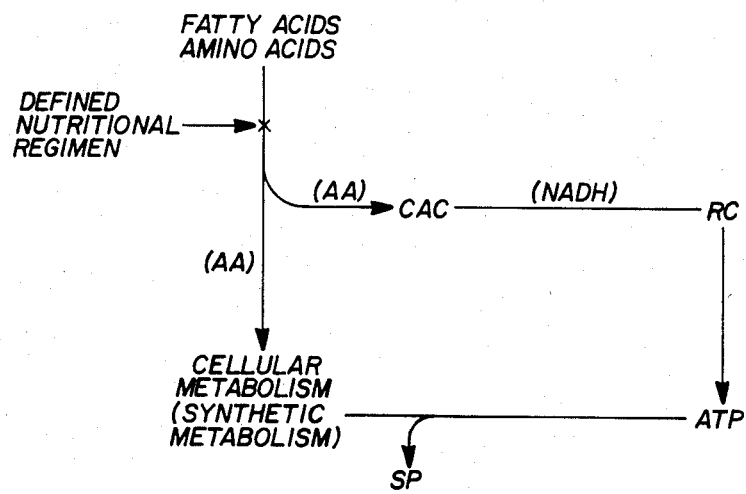
FIG. 3 is a flow diagram depicting the regulatory pathways of amino acid metabolism in malignant cells subjected to Dnr treatment of this invention.

The integrated mechanism by which cancer cells are selectively destroyed by the present therapy is schematically shown in FIGS. 3 and 4. With the imposition of only the Dnr (FIG. 3) of the present therapy, the only substantial source of ATP energy available to the cancer cell is amino acids from the dietary proteins, and this source is effectively minimized by the Dnr. However, the synthetic metabolism associated with cancer cell proliferation requires a high rate of intake of amino acids; consequently, the available amino acid supply is split between the direct metabolic needs and the ATP production needs (see FIG. 3). The ATP is therefore produced at a rate such that it satisfies the overall metabolic rate needs of the cancer cell (including, the synthetic metabolism associated with proliferation in the dividing cells, the basic essential metabolism, and the quite substantial requirements of the $Na^+$ outpumping), and the overall cellular metabolism will proceed at the rate permitted by the availability of ATP to provide the requisite energy for the hierarchy of reactions. These respective needs uniquely determine how much of the available amino acid intake will go into ATP production (via the CAC and the RC), and how much will go directly to cancer cell metabolism (including the energy used in the sodium pumps of the percellular membrane to keep $Na+$ adequately pumped out of the cell). The imposition of the Dnr alone will cause a slowed growth of the cancer cell due to the restricted intake rate of amino acids, but the available amino acids will be partitioned between cancer cell metabolism and ATP production in a balanced manner so that cancer cell proliferation continues, however slowly.

By means of the defined nutritional regimen imposed by the present therapy, the ability of the cancer cell to make ATP at a significant rate is greatly reduced, while the normal cells, which can readily utilize the abundant glucose of the Dnr, are unaffected. In essence, the cancer cell is selectively "starved" of its nutrients by the Dnr.

The Dnr of the present invention is individually defined for each patient in its total daily caloric content and in its composition (see section titled "Defined Nutritional Regimen (Dnr)", infra) based on Bmr and $Emr_A$ of the patient. In all cases, however, it must be substantially fat-free, providing only the minimal essential fatty acids, must provide only the amount of protein minimally required for maintenance of whole-body nitrogen balance when averaged over the treatment period, and must contain a level of carbohydrates adequate to raise the total Dnr daily caloric provision to an amount essentially equal to, but not in excess of, the 24-hour caloric requirement determined by the effective metabolic rate ($Emr_A$) of the patient measured under the daily treatment conditions. Vitamin and mineral requirements are added to the Dnr to sustain the patient's normal metabolic and life processes, but are unrelated to the oncolytic purposes of the therapy. Non-nutritive bran is also added to the Dnr to provide bulk and fiber. Essential fatty acid content in the Dnr consists of linoleic and linolenic acids, provided as a percentage of the daily caloric requirement determined by the basic $Emr_A$ of the patient, i.e., the $Emr_A$ level without an elevation in the Bmr. The daily protein level is specified on an individual-patient basis and the required carbohydrate is calculated so as to provide, after accounting for the fatty acid and protein caloric contributions, the balance of the total caloric requirement specified by the measured $Emr_A$.

Although the defined nutritional regimen (Dnr) constituting the first part of the present invention can be expected to reduce, significantly and selectively, the rate of generation of ATP in the cancer cell, it may not alone be sufficient to do more than significantly slow the rate of proliferation of the cancer cell, i.e., increase the $G_1$ period of the cell cycle while the cell is growing to mature size for subsequent division. The second part of the present invention (see FIG. 4) is consequently designed to insure that the net generation rate of ATP in the cancer cell will be still further reduced by the administration of a sufficient dosage of an uncoupling agent (UA), such as DNP, which reduces the rate of phosphorylation of ADP to ATP. Since normal cells in the patient can use the abundant glucose provided by the carbohydrate components of the Dnr for ATP production, administration of the appropriate dosage of uncoupling agent will not substantially affect their rate of ATP production, which will remain at the level required for the normal functioning of those cells. The coordinated administration of the uncoupling agent (UA) concurrently with the Dnr (see FIG. 4) according to the present invention, greatly decreases the net ATP production rate in the cancer cells. The use of the UA and Dnr together significantly reduces the formation of ATP from the potential energy available from the oxidation of the Dnr-limited amino acids supply in the CAC, wasting this energy as heat. Thus, the ATP pool of the cancer cell begins to decrease steadily immediately after the start of the present therapy, as the metabolic and sodium-pump utilization of ATP continues initially unabated. This ATP decline in the cancer cell is paralleled by an increase in cellular ADP, and the action of the RC is accelerated (i.e., more NADH per unit time is oxidized to $H_2O$ via the RC and the $O_2$ consumption rate is elevated proportionately) in the attempt to maintain the normal ATP level. This increased rate of NADH oxidation diverts amino acids in the cancer cell from synthetic metabolism into the citric acid cycle to make more NADH (see FIG. 4). In effect, the action of the UA in therapeutic dosage diverts the amino acid supply, already critically limited by the Dnr, from cancer cell metabolism into the CAC where they are oxidized, thus eventually stopping the synthetic metabolism of the cancer cell, while simultaneously lowering the net ATP production rate far below that needed just to support basal vital metabolism and $Na^+$ outpumping. As a consequence of these combined effects, the cancer cells ultimately tend to swell as net $Na^+$, $Cl^-$, and $H_2O$ enter due to the lack of ATP to power the $Na^+$ outpumping at an adequate rate. The combined effects of intracellular osmotic disruption and metabolic shutdown lead to the functional death of the cancer cells, which lyse and disintegrate.

Since the normal cells of the body readily utilize the abundant glucose provided in the present therapy by the Dnr, the net ATP production is substantially unaffected at therapeutic dosage levels of UA. Consequently, no diversion of normal cell amino acids to the CAC occurs, and normal metabolism and life processes proceed essentially unaltered in the normal (i.e., non-malignant) cells, although their rates of glucose and $O_2$ consumption are elevated. Thus, at therapeutic dosage levels of UA, no manifest source of normalcell toxicity maintains.

The basic action of DNP and other physiologically tolerable uncoupling agents is to effect the dissociation, via mechanisms not yet wholly understood (see Heytler, supra), of the normally coupled transfer of energy derived from the oxidation of NADH (and other minor substrates) by the RC to the formation of ATP by phosphorylation of ADP. In addition, it is known that DNP also stimulates the hydrolysis at a relatively low rate of already-formed ATP by activation of a mitochondrial ATPase [Hemker, supra], thus further reducing the net ATP availability in the cancer cells. Hence, the results of the clinical evaluation disclosed in this application, while ostensibly attributable in major part to the classical O/P uncoupling action of DNP [Heytler, P. G. supra], in combination with the prescribed nutritional regimen, may be at least partially attributable to less known, or as yet unknown, subsidiary effects of the practice of the invention.

In principle, any imposed agent or condition which effectively brings about the uncoupling of RC oxidation from ATP formation by phosphorylation of ADP comes within the classification of an "uncoupling agent" (UA) for the purposes and scope of the present invention. However, it is to be appreciated that many such UA, although producing quite effective O/P uncoupling, may not be clinically useable in the present invention because of their concomitant causation of specific toxic, or otherwise clinically detrimental or physiologically intolerable or undesirable, side effects. Such unwanted effects may be wholly or partially unrelated to the O/P uncoupling action of UA. DNP, the most preferred UA for use in the present invention, is substantially free of untoward side effects of any nature at the therapeutical dosages prescribed, when used with the prescribed Dnr in the coordinated therapy system of the present invention, as demonstrated in clinical trials. Detailed procedures for the determination and maintenance of safe dosage levels of DNP and other clinically suitable UA in humans are a fundamental part of the present therapy system (see section titled "Determination of Dosage Levels", infra).

Prior to administration of the present therapy system, each cancer patient should have a thorough evaluation of his or her past medical history and present condition to identify any potentially adverse factors which might affect individual ability to tolerate the oxygen and glucose uptake requirements of the therapy regimen at the therapeutical Bmr levels. Among the conditions requiring special consideration, in regard to the possible need for provision of ameliorative assistance during the therapy, are emphysema, reduced $O_2$-uptake rate capability (as in anemia and lung insufficiencies), circulatory insufficiencies, glucose absorption dysfunction, hypoglycemia, hyperglycemia, diabetes mellitus, liver dysfunction, and pronounced obesity.

It cannot be too heavily emphasized that the treatment of this invention should be attempted only by a thoroughly trained professional team including at least one professionally trained biochemist and one skilled professional in the oncology branch of medicine. The biochemist must have requisite experience and capability in interpreting and monitoring the individual daily test results and adjusting the individual treatment regimen to meet their exigencies in accordance with the invention. The oncologist must be thoroughly skilled in the monitoring and diagnosis of malignant conditions. Most preferably, the professional team will undergo an initial special training in the therapy of this invention before undertaking to administer such therapy to a human patient.

It should be further noted that, while the therapeutic principles described herein are clearly applicable to mammals generally, the treatment regimen as elucidated in detail hereinafter is of specific applicability only to humans and other mammals with comparable active and basal metabolic rate ranges—i.e. other primates. Specific adaptation of this invention to mammals with significantly higher or lower active and basal metabolic rate ranges is within the scope of this invention and can, using the principles herein described, be effected by those skilled in the requisite technology without departing from the invention. It is indeed contemplated that the therapy of the invention, with suitable adaptation to take account of the active and basal metabolism of the animal to be treated, will be particularly useful in the treatment of malignant conditions in valuable agricultural animals, pets, zoo animals, race horses and other pedigreed stock, etc.

Defined Nutritional Regimen (Dnr)

The nutritional regimen of the present invention must be carefully defined on an individual basis in regard to the fat, protein, carbohydrate, and total caloric content. The essential features of the Dnr of the present invention are the provision of (a) an absolute minimum of fat, which the cancer cells use for ATP-energy production, so as to supply substantially only the minimal level of essential fatty acids (Efa), (b) a minimum of protein, which the cancer cells use for ATP-energy production and for mitogenic anabolism, albeit an amount which is adequate on the average to maintain the whole-body nitrogen balance at minimal level during the overall treatment period, and (c) an allowance of carbohydrate (Cho) which, after subtraction of the total fat and protein caloric contributions, provides glucose sufficient to furnish the remaining daily calories required to satisfy the $Emr_A$, carefully calculated to avoid any substantial excess, since excess glucose would be converted to fatty acids which would then be readily available to the cancer cells for ATP-energy production.

In Phase I of the preferred treatment protocol (see "Typical Therapy System for Human Patients", infra), the essential fatty acids, protein, and carbohydrate components of the Dnr are derived from essentially pure sources or sources of precisely known analysis, and the Dnr is administered in the form of liquid-suspension cocktails at periodic intervals over the day. The preferred component sources are:

(1) for Efa: linoleic and linolenic acids at 1% of the patient's normal (non-elevated Bmr) $Emr_A$ from sources such as primrose oil, or a mixture of safflower and linseed oils, (2) for protein: casein or egg protein, and (3) for carbohydrate: a mixture of pure dextrose, sucrose, and starch. Non-nutritive bran (nominally 0.45 g/kg) may be added to the Dnr to provide fiber and bulk, along with the vitamin and mineral mix, prior to blending. The vitamin and mineral allowance also contains KCl (65 mg/kg) and NaCl (60 mg/kg), since the purified preferred sources supply very little K and Na, along with at least twice the Required Daily Allowance (RDA) of all water-and lipid-soluble vitamins, and appropriate levels of Ca, P, Mg, Zn, Mn, I, and Se, and choline.

In Phase II of the preferred treatment protocol, the Dnr is provided in specific solid-food menus of natural food elements of defined nutrient content formulated so as to give the $Pr_{min}$ level of protein, and as minimal an amount of fat as possible by the choice of low-fat food elements. The required carbohydrate allowance is composed of that occurring in the protein-supplying natural food elements, plus supplementation from substantially total-carbohydrate sources (candies, custards, and flavored carbohydrate beverages) to satisfy the total therapeutical $Emr_A$ caloric level necessary to an ambulatory patient or outpatient. Supplementary non-nutritive bran, if desired, and vitamins and minerals at the minimum RDA level or higher, are also provided in the completely specified Dnr for Phase II of the preferred protocol.

Although the oral route is preferred for administration of the Dnr, the use of parenteral alimentation procedures to administer substantially the nutrient equivalent of the Dnr in a form suitable for infusion can readily be used when clinical conditions so demand. In such cases, administration of amino acids in pure form (rather than as protein sources) is important. An example is the case where, because of a malignant growth blocking the esophagus, a patient cannot swallow even semi-solid foods or liquids at the start of the therapy. Once the tumor mass has been regressed by the therapy, and swallowing of the Dnr cocktails or tube-feeding is possible again, the preferred Dnr cocktail ingestion procedure can resume. Additionally, total or partial parenteral administration can be used for particular elements of the Dnr and/or particular vitamins and minerals which cannot be absorbed adequately when taken by the oral route in special patients.

For achieving the maximal rate of oncolysis and tumor regression, the preferred nutritional process of the present invention contemplates subjecting the patient to periodic abrupt decreases in protein intake while the Bmr is simultaneously at a substantially elevated level due to O/P uncoupling by the therapeutical uncoupling agent. By abruptly dropping the protein level from, e.g., Pr=25 g/70 kg body weight to Pr=5 g/70 kg body weight, but maintaining the total caloric intake required for total caloric balance by providing the appropriate increase in carbohydrate, a major sudden increase in the rate of ATP disappearance in the malignant cells is produced, with the ATP pool size of the normal cells remaining substantially unaffected.

A slower but continuous rate of oncolysis is effected by maintaining the protein intake steadily at the minimal level required to maintain the bodily nitrogen balance, and steadily maintaining a more moderate elevated-Bmr level by use of an uncoupling agent, while maintaining caloric balance with an appropriate intake level of carbohydrate. The somewhat slower, but steady malignancy regression rate obtainable with the Phase II protocol may be preferable to the "pulsed protein" rapid rate achievable with the Phase I protocol in some cases. In particular patients Phase I alone or Phase II alone may be preferred because of specific conditions unrelated to malignancy. Patients whose ability to support a Bmr level of 2.0 and above may be restricted because of preexisting physiological dysfunctions such as pronounced oxygen uptake insufficiency, circulatory impairment, glucose absorption blockage, and the like may do best on a mild regimen of the character described for Phase II.

It cannot be too heavily emphasized that the therapy of this invention must be carefully tailored to the individual patient, monitored carefully and readjusted as appropriate based on individual clinical indications.

In a preferred nutritional approach which will be generally appropriate for a significant segment of patients, the patient is first subjected to the pulsed-protein intake (Phase I) for substantially four such pulses, followed by a period of steady protein intake (Phase II). It will be understood that the precise regimen to be administered (Phase I alone, Phase II alone, or Phase I plus Phase II in tandem) in a particular case depends upon at least the Amr and therapeutical Bmr-accommodation capability of the patient, the urgency with which malignancy regression must be accomplished, and the mass of total malignancy burden to be regressed and may also depend upon any of numerous other factors, including other special physiological conditions or abnormalities of the patient.

Measurement of Metabolic Rates

The measurements of the oxygen consumption rate under basal and active conditions is of key importance in the therapy of the present invention. These measurements form the basis not only for quantitatively assessing the individual uncoupling effect of the UA, but also for precisely defining the total caloric requirement that the individual Dnr must satisfy. They thus permit the precise specification of the carbohydrate allowance which will meet the $Emr_A$ caloric need, without affording an excess of glucose, from which fatty acids useable by the cancer cells for energy purposes could otherwise be made. In this manner, inadvertent nutritional circumvention of the all-important direct glucoseutilization blockage, regarding ATP production via the RC, that innately exists in the malignant cells is prevented.

In the present therapy system, the $O_2$ consumption rate ($lO_2/d$) is determined using any of the variety of common methods and instrumentation currently available, e.g., the Collins respirometer. The Bmr, which indicates the minimal essential metabolic rate level, exclusive of muscular and other supplementary physiological activity (such as digestion), is measured following the standard medical protocol for basal metabolic rate determinations: measurement in the morning after a restful night's sleep and before any food is taken. The Amr, which indicates the metabolic rate of the patient under average normal active conditions, is measured by the same procedures as the Bmr, but with the particular patient carrying on his own normal average level of over-all activity. This measurement is usually performed in the midafternoon, but can be made at any time that provides a more accurate representation of the average activity level of the patient. The $Emr_A$ represents the effective or average 24hour metabolic rate, and is determined from the average of the measured Bmr and Amr: $Emr_A = \frac{1}{2}(Bmr + Amr)$.

In general, the Dnr and UA therapy, when concurrently and coordinately administered according to this invention, should raise the Bmr level to between about 1.3 and 3.0 times the Bmr shown in the Mayo Standard tables for a person of the same sex, height, weight, age, etc., preferably between about 1.3 and 2.3, in the initial treatment stage constituting, or akin to, Phase I. For Bmr levels much exceeding 2.5 times such rate for any extended period, (i.e. in the order of 1 day or more), it may not be possible for the patient to take in adequate Cho (in the Dnr) daily to meet the caloric demands due to the higher level of O/P uncoupling, although parenteral supplementary-glucose administration may be used to aid in negating or reducing any net caloric deficit. In general, since the rate of malignant cell oncolysis increases in relation to the increase in Bmr level and the simultaneous reduction of protein level in the coordinated Dnr, it is desirable to regulate the therapy to enable attainment of the maximal safe Bmr level for each individual patient during the interval of lowest protein intake. In Phase II, which is a follow-on phase in the preferred treatment regimen but may be the only treatment phase for some patients, the integrated regimen of the present invention is designed to yield a sustained Bmr level of between about 1.3 and 1.6 times the rate shown in the Mayo Standard tables, preferably about 1.5, while providing the lowest total daily fat intake possible, the lowest daily protein level which will still substantially permit a balance of body nitrogen to be maintained, and a net caloric balance over the whole of the Phase II treatment period.

Typical Therapy System for Human Patients

The preferred treatment protocol of the present invention, which will be useful with many patients, consists of two phases Phase I is administered on an "inpatient" basis., i.e. to a patient under continual supervised care and requires a treatment period of substantially four weeks, with the patient resident at a hospital or other treatment center where a specially trained therapy team which administers the therapy is located. Phase II may be administered on an "outpatient" basis to patients who have had Phase I treatment, with the patient visiting the treatment center at periodic intervals for laboratory tests, including metabolic rate determinations, and physical examinations. For patients who have not had Phase I treatment because they cannot tolerate the appreciably elevated basal metabolic rate levels thereof, a milder, but more extended, treatment regimen of Phase II alone may be administered.

Figure 5:
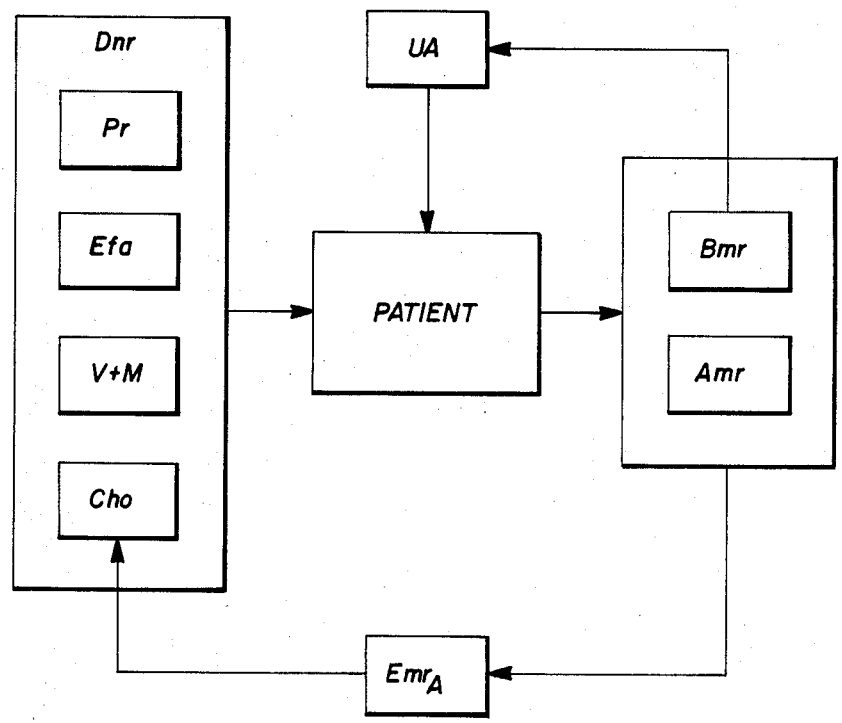
FIG. 5 is a schematic representation of the integrated system of interacting elements required for clinical implementation of the cancer therapy of the present invention.

The general scheme of Phase I of the therapy system is presented in FIG. 5. The patient is given the prescribed dosage D of UA, most preferably oral DNP, daily. Prior to UA administration and any food intake each day, the patient's basal metabolic rate (Bmr) is measured by the therapy technologists, normally in the early morning. Based on this Bmr reading, the UA dosage for the day is then adjusted, if necessary, to achieve and maintain the therapeutical Bmr level desired. The active metabolic rate (Amr) is also measured each afternoon, with the patient in his normally active state. The Bmr for a given day is combined with the Amr of the previous day to obtain the actual effective metabolic rate ($Emr_A$): $Emr_A(lO_2/d) = \frac{1}{2}(Bmr+Amr)$. The daily Dnr is then determined by a computer program which, in essence, calculates the amount of Cho (pure powder) necessary to provide the full caloric equivalent of the $Emr_A$ after accounting for the caloric contributions of the Pr and Efa-total fat components; the vitamin and mineral levels for the patient are also printed out. Since the daily Pr allowance is variable (see Table 1, infra), it is selected from a schedule previously stored in the computer, or entered as appropriate by the therapy coordinator. The Efa allowance for the particular patient is also specified in the overall Dnr computer printout for the day. Subsequently, the specific Dnr for the day for each individual patient is prepared by the therapy technologists who weigh out the required components from pure or fully defined nutrient sources and blend them with an adequate volume of water. The Dnr is then served in a series of liquid "cocktails" at periodic intervals over the course of the day. By this carefully integrated therapeutical system, the UA dosage and caloric allowance are determined and modulated daily to insure the achievement and precise caloric accommodation of the therapeutical Bmr and associated $Emr_A$ levels for complete patient safety and optimal oncolytic efficacy.

It is to be understood that the computer program can be replaced by appropriate graphs, charts and calculations.

A. Phase I

The treatment protocol for Phase I is designed to effect a maximum rate and extent of malignant cell reduction. In Phase I (see Table 1), the patient is initially administered a Dnr with Pr=15 for a period of seven days so that minimal protein steady-state conditions can be substantially reached and the $Pr_{min}$ under treatment conditions determined for the particular patient, using standard nitrogen-balance determination procedures. This important initial period has the added purpose of reducing the "excess" body-protein component, which might otherwise constitute a source of circulating amino acids useable by the malignant cells, to a minimum. During this period, a daily dosage of UA (DNP) is given, calculated for the patient such that a Bmr increase of minimally 50% (Bmr=1.5 times the Mayo Standard Bmr for the patient) is reached and maintained by daily monitoring and readjusting of dosage level as needed. On the eighth day, the protein level is elevated to Pr=30 and then decreased to Pr=25 for the following two days, with the daily dosage of DNP being so regulated as to hold the Bmr at about 1.5; some elevation of the Bmr above 1.5 will tend to occur near the end of this 3-day period. The Dnr protein level is then dropped to Pr=5 for the next two days, at which time the Bmr will escalate moderately but continuously; the DNP dosage is held at a low level during this period. The Bmr rise is held to a maximum of nominally 2.0 to 2.3 by providing a Dnr equal in caloric content to the $Emr_A$ corresponding to the maximum desired Bmr level. It is during this period when Pr=5 and Bmr=2.0 to 2.3 that a maximum rate of oncolysis is effected, with the protein restriction being maximum and the degree of uncoupling (as represented by the Bmr elevation) being simultaneously maximum. The protein is again raised to the 30, 25, and 25 levels for the next three days, followed again by two days at Pr=5, with the DNP level adjusted to give the desired Bmr levels in each period. This same cycle (a 3-day, elevated protein period followed by a 2-day, low protein period) is repeated twice more, for a total of four such cycles in Phase I.

During Phase I, the Dnr intake is determined daily as the specified protein intake $(Pr \times W_B)$+total fat (Efa)+Cho allowance. The Efa is given at about 1% of the $Emr_A$ kilocalories consumed in one day, at the unelevated Bmr condition. The Cho allowance is calculated by the formula: $Cho(lO_2/day) = Emr_A (Pr \times W_B)$−Total Fat, all expressed in terms of $lO_2/d$, wherein $Emr_A$ is determined by the formula $Emr_A (lO_2/day) = \frac{1}{2}(Bmr+Amr)$, after measuring the oxygen consumption rate in the afternoon of the previous day (Amr) and the oxygen consumption rate in the morning of the current day (Bmr). The $lO_2/d$ values for each component are then converted to their gram equivalents by standard caloric conversion factors.

After addition of 0.45 g/kg of non-nutritive bran and the vitamin and mineral mix (including 65 mg/kg of KCl and 60 mg/kg of NaCl), the Dnr mixture is blended with an appropriate volume of pure water (nominally, e.g., 20 ml/kg body weight) and refrigerated. The Dnr suspension is given in six equal-volume cocktails at equal intervals throughout the day. For example, it may be started at 9:00 AM, 11:00 AM, 1:00 PM, 3:00 PM, 5:00 PM and 7:00 PM, or for earlier rising patients the intervals can be adjusted to commence and end earlier. Alternatively, the cocktails may be given at 7:30 AM, 10:00 AM, 12:30 PM, 3:00 PM, 5:30 PM, and 8:00 PM or at any other convenient hours that afford equal spaced intervals between feedings. Of course, the cocktails could be given, e.g. 7 or 8 times per day instead of 6 times. Pancreatin (equivalent to 1 gram, USP) is given during periods of low protein intake as a digestive enhancement.

While the patient should be under fully supervised care during the administration of Phase I of the preferred therapy system, the patient may be fully ambulatory, depending upon his or her particular physical condition and capabilites. The patient's activities should in any case be moderate, with bed or chair rest available and availed of during periods when the Bmr is appreciably elevated (2.0 and above). For particular patients with oxygen uptake difficulties at high Bmr levels, administration of pure oxygen can be used to amplify oxygen availability. Upon completion of Phase I the patient, after a brief period to establish the constant daily DNP dosage for Phase II, may begin Phase II, either as an outpatient or under continued supervision. As already noted, an extended Phase II treatment may be preferred for some patients.

TABLE I

| Day | DNP given | Pr | Notes |
|---|---|---|---|
| 1 | Yes | 15 | Patient starts on Dnr based on $Emr_A$. Bmr, $W_B$, and Amr measurements are made daily throughout Phase I. |
| 2 | Yes | 15 | Dnr specified daily on basis of measured $Emr_A$ value ($lO_2/d$). |
| ↓ | ↓ | ↓ | |
| 6 | Yes | 15 | Urine collection (24-hour) begins. |
| 7 | Yes | 15 | Urine collection (24-hour) finished; 24-hour urine nitrogen content determined; $Pr_{min}$ calculated for patient. |
| 8 | Yes | 30 | |
| 9 | Yes | 25 | |
| 10 | Yes | 25 | |
| 11 | Yes | 5 | Cho allowance in Dnr for these days is pegged at the value corresponding to $Emr_A$ for the desired $Bmr_{max}$. |
| 12 | Yes | 5 | |
| [Repeat cycle of day 8 through day 12 three more times.] | | | |
| 28 | No | $Pr_{min}$ | DNP discontinued. Pr of Dnr is raised from Pr = 5 to $Pr_{min}$. |

B. Phase II

In the preferred therapy the patient starts Phase II as a "follow-on" phase immediately after completing the regimen of Phase I. The subject is given the Dnr in liquid form (the same as given in Phase I) with a protein content equal to the $Pr_{min}$ level ascertained for the patient at the 6 and 7th days of Phase I for few days while the steady daily dosage of DNP required to maintain a Bmr level between about 1.3 and about 1.5 is established. Following that, the patient may leave the treatment center and in any event commences taking the Dnr in the form of the defined solid-food regimen (supra), with P=$Pr_{min}$ and the total caloric intake level equivalent to the $Emr_A$ level estimated for the subject according to the particular activity level anticipated for the level of physical activity of the patient.

The daily nutritional regimen's $Pr_{min}$, fat, and carbohydrate allowances remain substantially the same each day during Phase II, in accordance with the daily menus and Cho supplements specified for the patient at the time that he commences the solid food regimen. The solid food regimen Dnr is in the form of meals of natural whole foods which have been carefully assayed for nutrient content in regard to protein, total fat, and carbohydrate. The basic dry ingredients (dehydrated and freeze-dried food items) for preparing each specified Dnr menu are prepared in preweighed and packaged form for each patient on a customized basis. The DNP daily dosage remains constant throughout Phase II unless adjustments are found necessary to maintain the therapeutical Bmr level. Phase II may run as long as needed. A period of about four weeks is a target on the preferred therapy, but Phase II may run longer or shorter. For patients unable to stand Phase I therapy, Phase II, and administration of Dnr in liquid form, may run for many weeks.

Uncoupling Agents

The functional purpose of oxidative phosphorylation O/P is the transfer of the energy of reducing equivalents resulting from the oxidative conversion of substrates in the CAC or elsewhere into ATP, the basic energy-supplying molecules of the cell, via the RC. By adding an O/P uncoupling agent to such an O/P system, the amount of phosphorylation of ADP to yield ATP is in effect reduced in relation to the concentration of the UA present. The $O_2$ consumption rate, however, is not only undiminished, but is generally accelerated because of the resulting deficit in the ATP production rate, which lowers the ATP pool size. The energy of the reducing equivalents which is lost due to the uncoupling action goes into heat, which is dissapated by the body via the normal radiation and evaporative cooling (sweating) mechanisms.

The most preferred uncoupler of the present invention is 2,4-dinitrophenol (DNP). Other uncoupling agents that are among those preferred are 2,6-dinitrophenol and 4,6-dinitrocresol. However, it will be understood that any one or any combination of an extensive array of O/P uncoupling agents may potentially be used for the cancer therapy system of this invention, at the appropriate doses, provided that they are physiologically tolerable by the patient and free of clinically toxic or detrimental side effects. Known uncoupling agents include, but are not limited to: 4-hydroxy-3,5-diiodobenzonitrile; benzotriazoles, such as 5-nitrobenzotriazole, 5-chloro-4-nitrobenzotriazole, or tetrachlorobenzotriazole; benzylidenemalononitriles, such as 4-hydroxybenzylidenemalononitrile [4-OH-BMN], 3,5-ditertbutyl-4-hydroxybenzylidenemalononitrile, 3,5-ditertbutyl-4-acetoxybenzylidenemalononitrile, or α-cyano-3,5-tertbutyl-4-hydroxycinnamic acid methyl ester; 1,3,6,8-tetranitrocarbazole,2,6-dihydroxyl1,1,1,7,7,7-hexafluoro-2,6-bis (trifluoromethyl)heptanone-4-[bis(hexafluororoacetonyl)acetone]; free fatty acids, such as long chain aliphatic monocarboxylic acids, n-tetradecanoic acid [myristic acid], or cis-9-octadecenoic acid [oleic acid]; phenols, such as 4-chlorophenol, 2,4,6-trichlorophenol] [TCP], 2,4,6-tribromophenol, pentachlorophenol [PCP], 4-nitrophenol, 2,4-dinitrophenol [DNP], 2,6-dinitrophenol [2,6-DNP], 4-isobutyl-2,6-dinitrophenol, 4-isooctyl-2,6-dinitrophenol, 4,6-dinitrocresol, or 2-azido-4-nitrophenol; phenylanthranilic acids, such as N-phenylanthranilic acid, N-(3-nitrophenyl)anthranilic acid, N-(2,3-dimethylphenyl) anthranilic acid [mefenamic acid], N-(3-chlorophenyl)anthranilic acid, or N-(3-trifluoromethylphenyl)anthranilic acid [flufenamic acid]; 2-(phenylhydrazono)nitriles, such as carbonyl cyanide phenylhydrazone (phenylhydrazonomalononitrile) [CCP], carbonyl cyanide 3-chlorophenylhydrazone [m-Cl-CCP;CCCP], carbonyl cyanide 4-trifluoromethoxyphenylhydrazone [p-$CF_3$O-CCP;FCCP], carbonyl cyanide 4-(6'-methyl-2'-benzothiazyl)-phenylhydrazone [BT-CCP], the methyl ester of phenylhydrazonocyanoacetic acid, the methyl ester of (3-chlorophenylhydrazono)cyanoacetic acid, 2-(3'-chlorophenylhydrazono)-3-oxobutyronitrile, 2-(2',4-dinitrophenylhydrazono)-3-oxo-4,4-dimethylvaleronitrile, or 2-[3',5-bis(trifluoromethyl)phenylhydrazono]-3-oxo-4,4-dimethylvaleronitrile; salicylanilides such as, salicylanilide, 2',5-dichloro-4'-nitrosalicylanilide [S-3], 4',5-dichloro-3-(p-chlorophenyl)salicylanilide [S-6], 2',5-dichloro-3-(p-chlorophenyl)-5'-nitrosalicylanilide [S-9], 2',5-dichloro-3-tert-butyl-4'-nitrosalicylanilide [S-13], 3,5-dichlorosalicylanilide, 3,5-dichloro-4'-methylsalicylanilide, 3,5-dichloro-4'-nitrosalicylanilide, or 3,4',5-trichlonitrosalicylanilide [DCC]; tribromoimidazole [TBI]; trifluoromethylbenzimidazoles, such as 2-trifluoromethylbenzimidazole [TFB], 5-chlorotrifluoromethylbenzimidazole [CTFB], 4,5-dichlorotrifluoromethylbenzimidazole, 4,7-dichlorotrifluoromethylbenzimidazole, 4,5,6-trichlorotrifluoromethylbenzimidazole, 4,5,6,7-tetrachlorotrifluoromethylbenzimidazole [TTFB], 4-(2-chlorophenylhydrazono)-3-methyl-5-isoxazolone, 3-acetyl-5-(4-fluorobenzylidene)-2,5-dihydro-4-hydroxy-2-oxothiophene, 2-amino-1,1,3-tricyano-1-propene, n-decylamine, anilinothiophenes, such as 2-(2,6-dimethylanilino)-3, 4-dinitro-5-chlorothiophene [DDCT], or 2-(4-chloroanilino)-3,4-dinitro-5-bromothiophene [BDCT], arsenate ion, arsenite ion, cadmium ion, 2-chloro-5-nitrobenzylidenemalononitrile, decachloro-1,2-carborane [decachloro-barene], desaspidin, diethylstilbestrol [stilbestrol, DES], gramicidin D, merphalan (sarcolysine), thyroxine, tetraphenylboron ion [TPB], trialkyltin ion, tributyltin ion, and valinomycin. As discussed previously (supra), for appropriate clinical use in the present therapy system, an O/P uncoupling agent must not only be capable of producing an adequate elevation of the Bmr to the prescribed therapeutic levels, but must also be substantially free of any detrimental, toxic, or otherwise significantly undesirable side effects, and must also be physiologically tolerable by the patient in order to be used in the therapy treatment of this invention.

As will be readily apparent, it is unlikely that, e.g. arsenic-containing UA or DES will fulfill all of the criteria for UA to be utilized in this invention.

The use of 2,4-dinitrophenol (DNP) as the uncoupling agent in the malignancy therapy system of this invention is particularly preferred and has many advantages. Of all the known O/P uncoupling agents, DNP is by far the most thoroughly investigated, having been used as the classic uncoupling agent of choice in number of a very great laboratory studies of O/P. The dosage-Bmr relationship for humans was initially studied by Cutting et al. [Cutting, W. C. et al. *J. Am. Med. Assoc.* 101, 193–195 (1933)], who demonstrated also the absence of any significant toxicity, even for periods of extended use for obesity reduction in humans, at dosage levels and treatment periods much greater than are called for in the present invention.

The toxicity symptoms exhibited by humans at overdosage levels are also well established. The half-time of DNP in the body is on the order of 12 hours, so that its Bmr-elevating effect declines relatively rapidly following cessation of administration. Moreover, the rate of Bmr elevation with increasing dosage is significantly lower than that of other O/P uncoupling agents which have been used in humans (e.g., 2,6-dinitrophenol and 4,6-dinitrocresol, among others) for obesity reduction, thus providing a higher margin of safety in clinical use. DNP is extremely stable and is not biotransformed or metabolized in the body, the intake being excreted almost quantitatively as DNP in the urine. Furthermore, DNP is inexpensive and is readily available in pharmacologically pure form.

Determination of Dosage Levels

The DNP dosage (mg/kg of body weight) to produce a desired steady Bmr level of 1.5 times the Mayo normal Standard level, for example, in an individual patient can be determined in the following fashion:

A daily DNP dosage known to raise the Bmr to approximately 1.5 times the Mayo normal Standard level (nominally 4.0 mg/kg body weight under normal protein intake levels) is given to the patient, until the Bmr plateaus. The Bmr actually produced by this steady dosage is then measured for that patient, and the appropriate dosage for producing the desired Bmr=1.5 is calculated using the relationship $$D_{1.5} = D_A \times 0.5 \times \left[ \frac{Bmr_A}{Bmr_S} - 1.0 \right]^{-1}$$

wherein $D_{1.5}$ is the required dosage of DNP for producing a Bmr=1.5, $D_A$ is the actual dosage of DNP given, $Bmr_A$ is the measured Bmr produced $D_A$, and $Bmr_S$ is the Standard Bmr taken from the Mayo Normal Standards [*Am. J. Physiology*, July 1936]. The $D_{1.5}$ is recalculated periodically by this procedure and administered so as to maintain the Bmr substantially steady at the desired 1.5 level.

More generally, the method used for determining the safe human dosage level of a clinically usable uncoupling agent to produce a desired Bmr level is to raise the UA dosage in small successive increments, allowing for attainment of a steady-state (plateau) Bmr level after each increment, until the desired therapeutical Bmr level is reached. Inasmuch as the O/P uncoupling effectiveness of any UA may be affected significantly by the physiological state of the particular patient and by the Dnr therapy, the determination and modulation of the particular dosage levels and the administration schedule in accordance with the present invention, at least in Phse I or other initial treatment stage, must be performed only by a specialized team of adequately trained individuals as aforementioned.

Characteristics of Malignant Cells and Effects of O/P Uncoupling Agents

Malignant cells are known to metabolize glucose to pyruvate through the Embden-Meyerhof Pathway, exactly as occurs in normal cells. However, instead of converting pyruvate to AcCoA (for subsequent oxidation in the citric acid cycle to produce NADH for fostering ATP production in the respiratory chain), pyruvate is converted substantially in toto to lactic acid, which is then excreted from the malignant cells. Although some ATP is generated by the oxidation of glucose in the EMP, the amount is only a very small fraction (about 6%) of the total ATP energy potentially available from the complete oxidation of glucose in the CAC and RC. Thus, malignant cells cannot effectively use glucose (the predominant source of ATP energy in normal cells) as an ATP energy source, and must rely chiefly upon citric-acid-cycle oxidation of AcCoA from fatty acids and AcCoA and CAC intermediates from amino acids for their basic ATP energy requirements. By direct intravenous administration of radioactively labelled glucose into malignant-bearing hosts, it has been shown that, in the malignant cells, the glucose is substantially converted to lactic acid, which is subsequently excreted from the cells into the circulation and that relatively little of the pyruvate from the initial glucose gets into the citric acid cycle to produce NADH for subsequent ATP production in the respiratory chain. [Busch, H. et al. *Cancer Research* 20, 50–57 (1960); Busch, H. *Cancer Research* 13, 789–794 (1955); Busch, H. et al. *J. Biol. Chem.* 196, 717–727 (1952); Nyhan, W. L. et al. *Cancer Research* 16, 227–235 (1957)]. Although the normal cells of some body organs like brain, heart and kidney also convert a large proportion of the glucose to lactate initially, the "lactate pool" so formed is rapidly converted back to pyruvate and used to produce AcCoA, which then enters the CAC for the normal metabolic processing and use; the lactate formed in malignant cells, however, is simply excreted in large measure. The copious excretion of lactate by malignant cells has been demonstrated in vivo in several cases by direct analysis of the lactate concentration in the blood before entering a malignant tumor and in the blood leaving the same tumor [Cori, C. F. et al. *J. Biol. Chem* 64, 11-22 (1925); Cori, C. G. et al. *J. Biol. Chem* 65, 397-405 (1925); Warburg, O. et al *Klin. Wochschr* 5, 829-832 (1926)]. Intravenous administration of labelled pyruvate, the final product of the Embden-Meyerhof Pathway which in normal cells is converted to AcCoA, resulted in the production of labelled lactate in the malignant cells in substantially greater quantities than in normal cells [Busch, H. *Cancer Research* 15, 365-374 (1955)]. Although the citric acid cycle is fully active in malignant cells (using fatty acids and amino acids usually available in abundance in the plasma under normal dietary conditions) the use of the glycolytic endproduct from glucose in the citric acid cycle is minor, the terminal pyruvate being excreted as lactate [Muramatsu, M. *Gann.* 52, 135-148 (1961)].

The importance of glucose in ostensibly mediating the restriction of AcCoA formation in the malignant cell is demonstrated by experiments wherein slices of malignant tumors were found to be capable of metabolizing pyruvate in the Citric Acid Cycle without glucose present, but converted substantially more pyruvate (and glucose) to lactic acid when glucose was also present [Busch, H. et al. *Cancer Research* 16, 175-181 (1956)]. These representative results demonstrate that when adequate levels of glucose are present, malignant cells cannot efficiently utilize glucose or any Embden-Meyerhof Pathway intermediates in the Citric Acid Cycle to generate NADH for supporting ATP production in the respiratory chain, or for synthesis via the Citric Acid Cycle of any metabolic intermediates; thus, substantially all such requirements of the malignant cells must be satisfied by fatty acids and amino acids supplied by the plasma, normally from amply available dietary sources.

The following table demonstrates the dramatic but transient increase in the respiratory chain activity (represented by the $O_2$ consumption rate) of malignant cells (mouse ascites tumor cells) produced by treatment with DNP, in vitro. The cells were maintained in Krebs-Ringer salt solution containing 0.2% glucose and the Citric Acid Cycle metabolic intermediate indicated, at 0.03M concentration. The $Q_{O_2}$ ($O_2$ consumption rate, $\mu lO_2$/mg cells/hr), equivalent in the whole-body case to the specific basal metabolic rate $Bmr/W_B$, was measured soon after the cells were placed in the respirometry flasks. Then DNP was added (39 $\mu$g/ml) and the maximum transient $Q_{O_2}$ (equivalent to the beginning of a decline in NADH availability for respiratory chain oxidation) was determined following this transient rise. [Data taken from Woods, M., *J. Nat. Cancer Inst* 17, 615 (1956)].

| Substrate Added | $Q_{O_2}$ before DNP added | Max. $Q_{O_2}$ after DNP added | $Q_{O_2}$ 46 minutes after DNP added |
|---|---|---|---|
| Glucose (only) | 5.8 | 20.2 | 1.0 |
| Citrate | 5.6 | 22.1 | 12.3 |
| Succinate | 6.1 | 22.5 | 14.2 |
| Malate | 6.1 | 24.9 | 8.8 |

When the malignant cells are first removed from the ascitic serum in which they grow in the body, and are placed in the Krebs-Ringer salt solution containing the substrate/glucose or glucose only, the cells continue for a time to utilize the internal pool of fatty acids and amino acids they possessed at the time of removal from the host animal, for ATP production (i.e. FA/AA→CAC→NADH→RC→ATP). The initial $Q_{O_2}$ values are thus essentially all the same. Then when DNP is added, there is a sudden and pronounced increase in the $O_2$ consumption rate, due to the increase in free ADP in the cells caused by the uncoupling of the phosphorylation factors in the respiratory chain.

The energy sources available in malignant cells are clearly not glucose because 46 minutes after DNP addition the residual $O_2$ consumption is much less in the presence of abundant glucose alone than in the presence of glucose plus a citric acid cycle intermediate, which can be used for energy-yielding oxidation When tumour size is substantially reduced, it is standard medical experience that substantial lysis of the malignant cells in the tumours has occurred. Lysis is generally known to accompany cell death and cell degeneration. The clinical studies of the present invention provide substantial evidence of tumour cell lysis and tumor regression, termed oncolysis.

Clinical Effects of Dnr and Uncoupling Agent Malignancy Therapy According to This Invention Four patients were treated according to Phase I and Phase II of the "Typical Treatment Protocol for Human Patients" of the detailed description, except that each phase extended for twelve days only. In addition, a rest period between phases was afforded, during which no DNP treatment was given. Four additional patients were treated in Phase I alone. Results were as hereinafter described:

Example 1

Case No. 1: Female, 54 years old.

Diagnosis: Adenocarcinoma (clinically colon); far advanced, infiltrating viscera; extensive liver metastases.

Basis of diagnosis: Ultrasound scans with biopsy of protrusive tumor mass; laparotomy with multiple histological specimens and analyses. (Tumor inoperable due to wide involvement).

Therapy prior to present treatment: None.

Tumor status at start of present treatment: Huge tumor mass occupying the epi- and mesogastrium region (X-ray); tumor compressing lower esophagus to near closure (barium esophagram), stomach compressed and displaced to left; left lobe of liver essentially replaced by tumor, right lobe with numerous metastases (liver scan); hard, fixed, palapable tumor mass measuring 10 cm (vertical)×7 cm (horizontal) protruding superficially from abdomen in region corresponding to left lobe of liver. Patient weak, thin, rapidly losing weight, pain and intense feeling of pressure in tumor area; able to swallow only liquids, which must be taken very slowly; stomach accommodates only small volume before feeling of satiation occurs. [Dimension and mass changes given in the following response-data tables are for the protruding 10 cm×7 cm abdominal tumor mass].

Response to treatment:

| | A. Phase I | | |
|---|---|---|---|
| Day | Tumor Dimension | % Reduction in Tumor Mass | Doctor's Progress Notes |
| 1 | 10.0 | — | Patient starts on Dnr; no DNP. |
| 2 | — | — | Patient starts on DNP. |
| 3 | — | — | Patient reports she is feeling much better; abdominal pain and pressure sensation are definitely decreasing; swallowing is easier. |
| 6 | 8.5 | 38.6 | Oncologist reports tumor is becoming softer in consistency. |
| 8 | — | — | Patient reports all pain and pressure sensations have disappeared; swallowing fully normal. |
| 10 | — | — | Oncologist reports tumor still decreasing in size; has become still softer in consistency. |
| 12 | — | — | Final day of Phase I treatment. Bmr was 2.24 during the final 16 hours of the period. |
| 13 | 6.0 | 78.4 | Patient in excellent condition; reports feeling fine. Vital signs, blood parameters all normal; tumor greatly shrunken, nonprotrusive, flat, difficult to palpate. No signs whatever of toxemia despite large initial tumor mass and rapid rate of tumor lysis on day 12. |
| 16 | 5.0 | 87.5 | Oncologist reports tumor has continued to shrink despite cessation of treatment and return to normal protein level; overall dimension has decreased 50%. |

The oncologist noted the following: X-rays, liver scan, and esophagram performed on day 18 indicated a pronounced decrease in the visceral tumor mass and liver metastases, with suggestive regeneration of normal liver tissue in previously metastatic sites, and essentially normal esophageal transport and emptying into stomach. Throughout the treatment period, the patient's blood pressure, pulse rate, temperature, and blood parameters remained stable and in the normal range. The DNP produced the intended transient increase in metabolic rate; no side-effects other than mild sweating due directly to the DNP, were observed. Patient's overall condition has improved greatly.

| | B. Phase II | | |
|---|---|---|---|
| Day | Tumor Dimension | % Reduction in Tumor Mass | Doctor's Progress Notes |
| 1 | 11.0 | — | Patient on Dnr with $Pr_{min}$ and DNP. Pain, with sensation of intense pressure within tumor region, swallowing difficult. |
| 3 | — | — | Patient reports swallowing is easier. Oncologist reports tumor softer and slightly decreased in size. |
| 5 | — | — | Patient reports abdominal pain much diminished. Oncologist reports tumor continuing to decrease in size; becoming flatter and less protrusive. |
| 6 | 7.0 | 74.2 | Patient reports feeling much better; abdominal pressure sensation much decreased as is fullness sensation; no pain in tumor region. Oncologist reports tumor now flat, non-protrusive; continuing to decrease in size. |
| 12 | 6.0 | 83.8 | Final day of treatment period (Phase II). Patient reports feeling fine; pressure sensation gone; swallowing normal. Vital signs, blood parameters normal. Oncologist reports tumor residue very soft, difficult to palpate. |
| 13 | — | — | Blood analyses reveal a significantly elevated level of lactic dehydrogenase (LDH) commensurate with the pronounced tumor lysis observed in the palpable tumor; the blood urea nitrogen level is normal. |

The oncologist noted the following: the patient's body weight remained stable throughout the treatment period, as did the serum total protein level; the red blood cell count increased from 3.9 to $4.1 \times 10^6$. On day 15, the patient ate normal meals of solid food without encountering swallowing or saturation problems of any kind; was in excellent general condition. Despite the extensive metastatic involvement of the liver, this patient experienced no digestive problems and was able to accommodate and assimilate the Dnr quite well, even at high caloric intake levels. The serum LDH level on day 13 was elevated nearly 10-fold, indicating the intensity of the tumor lysis of the preceeding days. Similarly indicative of the pronounced decrease in overall tumor activity was the fact that the blood urea nitrogen (BUN) level decreased 78% in this semicachexic patient over the "Phase I" treatment period.

The following table sets forth the DNP and Dnr treatment parameters for this patient, day by day in both treatment phases, and shows the results of Bmr and $Emr_A$ testing.

TABLE I

| Case No. 1: Daily Treatment Conditions | | | | | | |
|---|---|---|---|---|---|---|
| Day (No.) | DNP (mg/kg) | Pr (g) | Efa (ml) | Cho (g) | Bmr (lO₂/d) | $Emr_A$ (lO₂/d) |
| A. Phase I | | | | | | |
| 1 | 0 | 13.3 | 3.3 | 692 | not measured | 493 |

TABLE I-continued

Case No. 1: Daily Treatment Conditions

| Day (No.) | DNP (mg/kg) | Pr (g) | Efa (ml) | Cho (g) | Bmr ($lO_2/d$) | $Emr_A$ ($lO_2/d$) |
|---|---|---|---|---|---|---|
| 2 | 1.5 | 13.3 | 3.3 | 459 | 280 | 364 |
| 3 | 1.5 | 13.3 | 3.3 | 459 | 311 | 364 |
| 4 | 0.75 | 13.3 | 3.3 | 559 | 424 | 439 |
| 5 | 0.5 | 13.3 | 3.3 | 595 | 455 | 466 |
| 6 | 1.0 | 13.3 | 3.3 | 614 | 390 | 480 |
| 7 | 1.0 | 13.3 | 3.3 | 587 | 408 | 460 |
| 8 | 1.0 | 22.1 | 3.3 | 522 | 390 | 491 |
| 9 | 0 | 22.1 | 3.3 | 719 | 464 | 570 |
| 10 | 0.5 | 14.5 | 3.3 | 631 | 425 | 530 |
| 11 | 0 | 5.2 | 3.3 | 631 | 493 | 575 |
| 12 | 0 | 8.4 | 3.3 | 719 | 625 | 713 |
| B. Phase II | | | | | | |
| 1 | 4.5 | 10.5 | 1.2 | 477 | 378 | 455 |
| 2 | 4.0 | 10.5 | 1.2 | 484 | 362 | 460 |
| 3 | 0 | 45.1 | 1.2 | 503 | 504 | 510 |
| 4 | 0 | 19.1 | 1.2 | 559 | 366 | 525 |
| 5 | 0 | 12.4 | 1.2 | 534 | 389 | 500 |
| 6 | 0.5 | 10.5 | 1.2 | 537 | 317 | 500 |
| 7 | 0.5 | 7.4 | 0 | 559 | 331 | 510 |
| 8 | 1.0 | 8.4 | 1.2 | 527 | 304 | 490 |
| 9 | 1.0 | 8.4 | 1.2 | 554 | 355 | 510 |
| 10 | 2.0 | 8.4 | 1.2 | 574 | 306 | 525 |
| 11 | 2.5 | 5.6 | 1.2 | 601 | 317 | 510 |
| 12 | 0 | 9.1 | 3.3 | 659 | 324 | 510 |

EXAMPLE 2

Case No. 2: Male, 57 years old.

Diagnosis: Epidermoid carcinoma of the larynx (left supraglottic fold and false cords); metastasized to the left neck.

Basis of diagnosis: Direct laryngoscopy with multiple biopsies; biopsy of neck metastasis; CT scan and Xerographs of larynx and neck.

Therapy prior to present treatment: None.

Tumor status at start of present treatment: Large tumor of the left supraglottic fold infiltrating the false cords, but not crossing the midline; 2 cm diameter, hard, fixed, protruding metastasis in the left neck, causing severe steady submaxillar pain due to pressure on nerve. Patient unable to eat solid foods because of intense pain on swallowing, even liquids cause much pain; voice hoarse; moderately advanced emphysema of both lungs. [Dimension and mass changes given in the following response-data tables are for the protruding 2 cm. diameter metastasis in the left neck.]

Response to treatment:

A. Phase I

| Day | Tumor Dimension | % Reduction in Tumor Mass | Doctor's Progress Notes |
|---|---|---|---|
| 1 | 2.0 | — | Patient begins on Dnr; no DNP. Blood parameters (including serum total protein level), liver function tests, urinalysis, and vital signs all normal. |
| 1 | 2.0 | — | Patient has difficulty swallowing because of throat pain; also suffers from intense pain due to pressure on nerve from neck metastasis. Oncologist reports neck tumor hard, fixed, extremely painful. |
| 2 | — | — | Patient starts with DNP. |
| 3 | — | — | Patient reports intense pain in left neck; radiates to left ear. |
| 6 | — | — | Patient reports pain in left neck has diminished. |
| 9 | — | — | Patient reports pain in left neck has continued to diminish; feels that neck tumor is definitely decreasing in size. Oncologist has not measured tumor because of pain upon palpation. |
| 11 | — | — | Patient's Bmr increased to 2.97 and remained elevated during whole day. |
| 12 | — | — | Final day of treatment period (Phase I). Bmr decreased to 2.57, but remained above 2.0 for the remainder of the day. DNP discontinued yesterday. |
| 13 | 1.0 | 87.5 | Patient is greatly improved; reports feeling much better. Vital signs all normal. Neck tumor is much less painful upon palpation. Oncologist reports neck tumor drastically decreased over two-day period of elevated Bmr (87.5% decrease in total tumor mass); tumor much softer in consistency. |
| 14 | — | — | Patient reports pain has essentially disappeared in neck, but throat is "sore" at site of primary. Vital signs and blood parameters all normal; Bmr = 1.0. Patient feels fine; appetite very good. |
| 18 | 0.8 | 93.6 | Onocologist reports neck tumor residue slightly mobile, nonprotrusive, hardly palpable; nonpainful. Former hoarseness of voice (dysphonia) has greatly diminished. |

The oncologist noted the following: throughout the treatment period the patient's body weight, blood pressure, pulse rate, resipratory rate, temperature, and blood cytological and chemical parameters remained stable and within the normal range. The DNP produced the intended increase in metabolic rate; no side-effects due dirctly to the DNP were observed. Despite the fact that this patient had moderately advanced emphysema in both lungs, the elevation of the Bmr to as high as 2.97 produced no symptoms of respiratory insufficiency.

B. Phase II

| Day | Tumor Dimension | % Reduction in Tumor Mass | Doctor's Progress Notes |
|---|---|---|---|
| 1 | 4.0 | — | Tumor is hard, fixed, immobile, and very painful on palpation; patient is put on $Pr_{min}$ and DNP (4.5 mg/kg). |
| 5 | 1.0 | 98.4 | Neck tumor greatly diminished as is the pain associated with it; burning sensation at site of internal primary, especially upon swallowing. Patient feels very good otherwise; takes Dnr well. |
| 6 | — | — | Voice hoarseness much diminished. |
| 8 | 0.8 | 99.2 | Neck tumor residue hardly palpable; difficult to find; painless. Throat soreness at site of internal primary upon swallowing cold liquids, but no pain with warm liquids or warm semi-solid food. |
| 8 | 0.8 | 99.2 | Laryngoscopy of primary site reveals a small, nonbleeding, ulcerative lesion on the left supra-glottic fold, with surrounding inflammation. Patient feels fine; vital signs normal; Bmr = 1.27. |
| 11 | (nonpalpable) | — | Voice much clearer; throat pain less upon swallowing. Patient feels fine; is very hungry. |
| 13 | (nonpalpable) | — | Final day of treatment (Phase II); DNP discontinued after today. Patient is asymptomatic; feels fine; very hungry; only slight pain at primary site. |
| 16 | (nonpalpable) | — | Patient returns to solid food; no pain in throat after first 3 swallows; feels fine. |

The oncologist noted the following: Throughout the treatment period the patient's body weight, blood pressure, pulse rate, respiratory rate, temperature, and blood cytological and chemical parameters remained clinically stable and within the noraml range. The DNP produced the intended increase in metabolic rate; no side-effects whatever due to the DNP were observed.

Table II, below, summarizes the precise daily treatment conditions and measured metabolic rates for this patient.

TABLE II

Case No. 2: Daily Treatment Conditions

| Day (No.) | DNP (mg/kg) | Pr (g) | Efa (ml) | Cho (g) | Bmr ($lO_2/d$) | $Emr_A$ ($lO_2/d$) |
|---|---|---|---|---|---|---|
| | | | A. Phase I | | | |
| 1 | 0 | 11.0 | 2.91 | 580 | not measured | 452 |
| 2 | 1.5 | 11.0 | 2.91 | 411 | 304 | 325 |
| 3 | 1.5 | 11.0 | 2.91 | 411 | 340 | 325 |
| 4 | 1.0 | 11.0 | 2.91 | 531 | 439 | 415 |
| 5 | 1.5 | 11.0 | 2.91 | 640 | 409 | 497 |
| 6 | 1.5 | 11.0 | 2.91 | 644 | 318 | 500 |
| 7 | 1.0 | 11.0 | 2.91 | 637 | 389 | 495 |
| 8 | 1.0 | 18.4 | 2.91 | 583 | 431 | 540 |
| 9 | 0 | 18.4 | 2.91 | 804 | 520 | 629 |
| 10 | 0 | 10.9 | 2.91 | 768 | 601 | 650 |
| 11 | 0 | 3.0 | 2.91 | 768 | 901 | 895 |
| 12 | 0 | 11.0 | 2.91 | 770 | 781 | 830 |
| | | | B. Phase II | | | |
| 1 | 4.5 | 7.1 | 0.8 | 395 | 265 | 350 |
| 2 | 4.5 | 7.1 | 0.8 | 408 | 259 | 360 |
| 3 | 4.0 | 7.1 | 0.8 | 489 | 263 | 420 |
| 4 | 0 | 35.3 | 0.8 | 397 | 313 | 380 |
| 5 | 0 | 7.1 | 0.8 | 461 | 251 | 400 |
| 6 | 1.5 | 7.1 | 0.8 | 422 | 274 | 370 |
| 7 | 2.0 | 7.1 | 0.8 | 538 | 262 | 450 |
| 8 | 2.5 | 2.4 | 0 | 525 | 307 | 465 |
| 9 | 3.0 | 6.3 | 0.8 | 562 | 278 | 480 |
| 10 | 3.0 | 4.8 | 0.8 | 537 | 280 | 460 |
| 11 | 3.5 | 4.8 | 0.8 | 576 | 278 | 490 |
| 12 | 3.5 | 2.6 | 0.8 | 593 | 298 | 500 |

EXAMPLE 3

Case No. 3: Female, 51 years old.

Diagnosis: Lymphocytic lymphoma (nodular, mixed-cell type); retroperitoneal; infiltrating; far advanced.

Basis of diagnosis: Laparotomy with multiple biopsies; CT scans.

Therapy prior to present treatment: Extensive conventional mitoxin chemotherapy; laetrile.

Tumor status at start of present treatment: Huge retroperitoneal tumor mass with hard, fixed, nonpainful portion 14 cm (vertical)×10 cm. (lateral) protruding superficially in the epi- and mesogastrium region; protruding mass easily palpable, with well defined margins; central tumor mass displacing viscera outwards and downwards; liver, lungs, lymph nodes and marrow negative for metastases; blood free of blast cells. Patient extremely thin (cachexic), pale, anemic, tired, nervous; blood pressure slightly below normal (110/60); reports strong sensation of pressure in tumor region; severe abdominal pain at times; lumbar spinal pain, often radiating into legs. [Dimension and mass changes given in the following response-data tables are for the superficially protruding 14 cm.×10 cm. tumor mass.]

Response to treatment:

A. Phase I

| Day | Tumor Dimension | % Reduction in Tumor Mass | Doctor's Progress Notes |
|---|---|---|---|
| 1 | 14.0 | — | Patient begins on Dnr; no DNP. |
| 2 | — | — | Patient begins on DNP; complains of allergy activation (skin rash) because of corn-containing food she ate just prior to day 1; claims long-standing allergy to corn products. |
| 9 | 14.0 | — | Some pain in lower back; patient's Bmr has increased to therapy level (1.68) for first time. |
| 11 | 14.0 | — | Patient reports all pain has subsided; all pain medication stopped; |

A. Phase I -continued

| Day | Tumor Dimension | % Reduction in Tumor Mass | Doctor's Progress Notes |
|---|---|---|---|
| | | | blood test shows anemia has improved; allergy symptoms completely gone; Bmr = 1.68. |
| 12 | — | — | Final day of treatment (Phase I); Bmr has increased to 2.47. |
| 13 | 8.5 | 77.6 | Patient feels much better; all pain has diminished greatly; pressure sensation in tumor region has disappeared. Vital signs, blood parameters normal. Bmr = 1.0. Hemoglobin has increased 16% since starting treatment. Oncologist reports dramatic decrease in tumor size in just one day at elevated Bmr (2.47); tumor much softer; no longer protrusive; difficult to palpate. |
| 14 | 5.5 | 93.9 | Patient in excellent state; feels very happy; has much more energy. Blood parameters normal except serum total protein level still slightly low. Oncologist reports abdominal tumor mass has continued to decrease in size; has regressed inward and is very difficult to palpate; dramatic rate and extent of tumor reduction verified independently by three different oncologists. |
| 18 | — | — | Patient in excellent state; no pain whatever; vital signs all normal. Oncologist reports X-rays of abdomen show tumor opacity much reduced; viscera seen more clearly. |
| 20 | (see progress note) | — | Patient in excellent condition; good appetite; skin and mucosal color much improved; pain free. Oncologist reports previously protrusive residue still decreasing; is much softer; has sunk inward; residue can be detected only with deep palpation. |

The oncologist noted the following: Throughout the treatment period the patient's body weight, blood pressure, pulse rate, respiratory rate, temperature, and blood cytological and chemical parameters remained stable and within the normal range. The DNP produced the intended transient increase in metabolic rate; no side-effects due to the DNP were observed. Although this patient did not reach the desired therapy Bmr elevation of 1.5 until the 9th day of the treatment (which slowness is now known to be due to the initially cachexic condition) and attained a Bmr greater than 2.0 for only the last 18 hours of the Pr=15 period, the oncolytic responsiveness of the tumor during this short period was dramatic. Despite the great rate of oncolysis (93.9% reduction in tumor mass in only 3 days) and extensiveness of the tumor mass, the patient exhibited no symptoms of oncolytic toxemia. Pronounced toxemia would normally have been expected under such conditions but, on the contrary, the patient was in a greatly improved state (physically and mentally), with normal vital signs and blood parameters.

B. Phase II

| Day | Tumor Dimension | % Reduction in Tumor Mass | Doctor's Progress Notes |
|---|---|---|---|
| 1 | 11.0 | — | Patient with Dnr with $Pr_{min}$ and DNP; strong pressure sensation in central tumor site; feels very weak. |
| 4 | (see progress note) | — | Patient reports diminishing of pressure sensation in tumor site; some back pain. Oncologist reports tumor appears to be decreasing in size and becoming softer; no measurement given. |
| 6 | — | — | Patient reports pain minimal. Vital signs normal, except blood pressure which is characteristically low (90/60). |
| 9 | 8.0 (see progress note) | 61.5 (see progress note) | Oncologist reports tumor shape is changing; can now palpate what feels like individual lymph nodes; difficult to palpate tumor as it appears to be breaking up and flattening out; 8 cm. is maximum extent of flattened residue. |
| 13 | — | — | Final day of treatment period (Phase II); patient reports minimal pain; slept well. |
| 14 | Unmeasureable | (see progress note) | Oncologist reports tumor has lost shape and coherency; former mass seems to be disintegrating; more mobile; much softer consistency. |
| 15 | (see progress note) | (see progress note) | Oncologist reports tumor residue very ill defined and flattened; maximum dimension of diffuse residue is 7.5 cm. Patient resumed eating regular food without any problem; hemoglobin has increased 24.8% over initial level; blood parameters are normal including platelet concentration; blood is free of blast cells. |

The oncologist noted the following: Throughout the treatment period the patient's body weight, pulse rate, respiratory rate, temperature, and blood cytological and chemical parameters remained stable and within the normal range; the blood pressure was slightly below normal, as is characteristic for this patient. The DNP produced the intended increase in metabolic rate; no side-effects due to the DNP were observed. The average dosage of DNP over the 13 day treatment period was only 2.0 mg/kg; the average Bmr was correspondingly low, 1.30. Still, in the presence of the relatively low daily protein intake (average Pr=19.8), the tumor regressed rapidly and ultimately underwent a generalized disintegration; the blood remained entirely free of tumor cells during this disintegration. Even with the reduced level of protein in the Dnr, the hemoglobin increased 24.8%.

Table III below summarizes the daily treatment conditions and metabolic measurements of this patient:

TABLE III

Case No. 3: Daily Treatment Conditions

| Day (No.) | DNP (mg/kg) | Pr (g) | Efa (ml) | Cho (g) | Bmr ($lO_2/d$) | $Emr_A$ ($lO_2/d$) |
|---|---|---|---|---|---|---|
| A. Phase I | | | | | | |
| 1 | 0 | 9.5 | 4.1 | 437 | not measured | 342 |
| 2 | 1.5 | 9.5 | 4.1 | 302 | 259 | 240 |
| 3 | 1.5 | 9.5 | 4.1 | 302 | 278 | 240 |
| 4 | 1.5 | 9.0 | 4.1 | 329 | 294 | 284 |
| 5 | 2.0 | 9.0 | 4.1 | 499 | 297 | 388 |
| 6 | 1.5 | 9.0 | 4.1 | 509 | 301 | 395 |
| 7 | 1.5 | 9.0 | 4.1 | 382 | 346 | 300 |
| 8 | 1.5 | 15.1 | 4.1 | 445 | 318 | 414 |
| 9 | 0 | 15.1 | 4.1 | 586 | 435 | 460 |
| 10 | 0.5 | 7.6 | 4.1 | 480 | 392 | 407 |
| 11 | 0 | 1.1 | 4.1 | 480 | 437 | 454 |
| 12 | 0 | 4.0 | 4.1 | 533 | 640 | 527 |
| B. Phase II | | | | | | |
| 1 | 4.5 | 4.7 | 0 | 242 | 225 | 270 |
| 2 | 4.5 | 4.7 | 0 | 262 | 244 | 285 |
| 3 | 4.0 | 2.2 | 1.0 | 329 | 226 | 335 |
| 4 | 0 | 29.7 | 1.0 | 298 | 295 | 340 |
| 5 | 0 | 5.9 | 1.0 | 353 | 249 | 355 |
| 6 | 0 | 4.7 | 0.5 | 347 | 255 | 350 |
| 7 | 0.3 | 2.8 | 0.5 | 363 | 223 | 340 |
| 8 | 1.0 | 0 | 0 | 340 | 209 | 350 |
| 9 | 1.25 | 0.42 | 0 | 341 | 215 | 340 |
| 10 | 2.0 | 1.6 | 0 | 319 | 205 | 325 |
| 11 | 3.0 | 1.6 | 0 | 346 | 223 | 340 |
| 12 | 3.5 | 1.6 | 0 | 488 | 220 | 413 |
| 13 | 2.0 | 6.0 | 2.2 | 540 | 235 | 415 |

EXAMPLE 4

Case No. 4: Male, 59 years old.

Diagnosis: Adenocarcinoma of the prostate (moderately differentiated); infiltrating periprostatic soft tissue, lymph nodes, and wall of urinary bladder, widely disseminated bone metastases.

Basis of diagnosis: Cystoscopy with multiple biopsies; right pelvic lymph node dissection with histological analyses; transurethral resection with histological analyses; nephrogram; bone scans.

Therapy prior to present treatment: Laetrile, vitamin A, enzymes (IV, orally); hormone therapy; surgery (TURP).

Tumor status at start of present treatment: Greatly enlarged, rock-hard, malignant prostate; with tumor widely infiltrating periprostatic soft tissue, including wall of urinary bladder; left kidney semi-occluded due to tumoral obstruction of left ureter at point of entrance into bladder; multiple, widely disseminated bone metastases in cervical, dorsal, and lumbar spine, right, scapula, both iliacs, and both femurs. Patient still in good general condition; no pain, good appetite; moderately obese; chronic hypertension; frequent night and day urinations due to tumor pressure on bladder; difficulty in urinating; urine stream flow greatly reduced; acid phosphatase level nearly twice the normal maximum Response to treatment:

| | A. Phase I | |
|---|---|---|
| Day | Indications of Tumor Status/Response | Doctor's Progress Notes |
| 1 | Acid phosphatase level nearly double the normal maximum. | Patient starts on Dnr; no DNP. |
| 2 | — | Patient starts |
| 4 | — | on DNP. Patient's BMR rises to 1.4; vital signs normal; very good appetite. |
| 6 | Night urinations have decreased to 1; starting and maintaining urine flow easier. | Patient feels fine, Bmr = 1.52; blood pressure elevated due to characteristic hypertension. |
| 9 | — | Patient feels fine; vital signs normal, except blood pressure still elevated; moderate pain in back when lying in bed, disappears in walking. |
| 11 | — | Patient feels fine; Bmr = 1.98, blood pressure has decreased with diuretic. |
| 12 | — | Final day of treatment period (Phase I) patient reports sweating episode during previous night, temperature normal; Bmr = 2.30 today. |
| 13 | Urine flow significantly improved; stream stronger and more steady. | Patient reports he feels great; all pain has disappeared vital signs are normal, except elevated blood pressure which continues to decrease with diuretic. |
| 14 | Oncologist reports rectal examination shows prostate size has decreased, and consistency is not as hard as originally; acid phosphatase is significantly elevated, 5.3 times normal maximum, due to release from lysed prostatic cells. | Patient reports he feels great; asymptomatic; blood pressure and blood parameters normal, including serum total protein level. |
| 15–21 | Urination continues to improve despite cessation of treatment and resumption of increased protein intake; urination stream steady. | Patient continues to feel fine; entirely asymptomatic. |
| 22 | Bone scan shows significant reduction of bone metastases; onocologist reports excellent response to treatment period. | Patient continues asymptomatic; blood pressure under control with diuretic. |

The oncologist noted the following: Throughout the treatment period the patient's body weight, pulse rate, respiratory rate, temperature, and blood cytological and chemical parameters remained stable and within normal range; the characteristically elevated blood pressure was controlled with the use of a diuretic. The DNP produced the intended transient increase in metabolic rate; no side-effects due to the DNP per se were observed. The patient remains pain-free and in excellent general condition.

| | B. Phase II | |
|---|---|---|
| Day | Indications of Tumor Status/Response | Doctor's Progress Notes |
| 1 | Prostate much enlarged and very hard. | Patient on Dnr with $Pr = Pr_{min}$ and DNP; general condition good; moderate pelvic pain. |
| 4 | Oncologist reports prostate decreasing in size and becoming softer in consistency. | Patient reports pelvic pain has ceased entirely; feels fine. |
| 5 | Patient reports easier to commence urine flow; has new sensation that bladder now empties completely upon urination. | Patient reports greater volume of urine excreted per urination than before treatment started; feels fine. |
| 8 | Oncologist reports prostate is becoming flatter, more like normal shape. Patient reports stronger urination stream. | Patient asymptomatic; vital signs normal; blood pressure holding at 170/90 with diuretic. |
| 9 | Oncologist reports prostate is flatter and softer | Patient asymptomatic; feel fine. |
| 13 | Oncologist reports prostate still flatter and softer, especially on left side; former vesicle tenesmus has disappeared. Patient reports still better urine flow, without interruption; night urination frequency much less | Final day of treatment period (Phase II); DNP administration ceased today. |
| 15 | Oncologist reports prostate even flatter and softer, with pronounced change on left side; nonpainful; steady regression toward normal prostate size. Hemoglobin level has increased 13.4% over the initial level; classically, prostate cancer patients always exhibit anemia Additionally, the acid phosphatase level (classically taken as the most sensitive indicator of prostate tumor cell activity) is now completely normal. | Patient in excellent condition; asymptomatic. |

The oncologist noted the following: Throughout the treatment period the patient's body weight, pulse rate, respiratory rate, temperature, and blood cytological and chemical parameters remained stable and within the normal range; the characteristically high blood pressure was controllable with diuretics. The DNP produced the intended increase in metabolic rate; no side-effects due to the DNP were observed. Prostate cancer cells generally proliferate only very slowly, and hence possess a relatively low level of cellular metabolism; still, the tumor burden of the present subject regressed steadily with the present treatment. Equally significant is the fact that the patient was also moderately obese, wherein the malignant cells were given a strong survival advantage via the availability of a nonprotein energy source; yet, the present treatment was still able to impose a steady and effective rate of oncolysis. The previously elevated acid phosphatase level, the standard indicator of prostate tumor activity, became completely normal. Even with the protein intake reduced to the equilibrium level, the hemoglobin increased 13.4%. The pronounced increase in urine volume that was experienced is indicative of a removal of the left urethral tumor obstruction; similarly, the return of the sensation of complete emptying of the bladder correlates directly with the palpable reduction in the circumurethral tumor/prostate mass.

Table IV summarizes actual daily treatment for this patient.

TABLE IV

| Case No. 4: Daily Treatment Conditions | | | | | | |
|---|---|---|---|---|---|---|
| Day (No.) | DNP (mg/kg) | Pr (g) | Efa (ml) | Cho (g) | Bmr ($lO_2/d$) | $Emr_A$ ($lO_2/d$) |
| A. Phase I | | | | | | |
| 1 | 0 | 14.6 | 3.8 | 737 | not measured | 571 |
| 2 | 1.5 | 14.6 | 3.8 | 540 | 412 | 428 |
| 3 | 1.5 | 16.5 | 4.4 | 617 | 474 | 488 |
| 4 | 1.0 | 16.5 | 4.4 | 566 | 581 | 450 |
| 5 | 1.5 | 16.5 | 4.4 | 762 | 584 | 597 |
| 6 | 1.0 | 16.5 | 4.4 | 762 | 628 | 597 |
| 7 | 1.0 | 16.5 | 4.4 | 767 | 628 | 600 |
| 8 | 0.5 | 27.6 | 4.4 | 716 | 677 | 670 |
| 9 | 0 | 27.6 | 4.4 | 884 | 719 | 702 |
| 10 | 0 | 20.0 | 4.4 | 808 | 707 | 670 |
| 11 | 0 | 8.3 | 4.4 | 808 | 814 | 814 |
| 12 | 0 | 11.5 | 4.4 | 866 | 950 | 889 |
| B. Phase II | | | | | | |
| 1 | 4.5 | 15.3 | 4.2 | 594 | 444 | 550 |
| 2 | 4.5 | 15.3 | 4.2 | 615 | 415 | 565 |
| 3 | 4.0 | 15.3 | 4.1 | 635 | 409 | 580 |
| 4 | 0 | 60.6 | 4.1 | 600 | 562 | 600 |
| 5 | 0 | 20.6 | 4.1 | 665 | 463 | 610 |
| 6 | 2.0 | 15.3 | 4.1 | 678 | 418 | 615 |
| 7 | 2.5 | 15.3 | 4.1 | 678 | 429 | 615 |
| 8 | 2.5 | 15.3 | 0 | 711 | 465 | 630 |
| 9 | 3.0 | 14.2 | 2.0 | 677 | 435 | 610 |
| 10 | 3.0 | 17.2 | 2.0 | 751 | 463 | 650 |
| 11 | 3.5 | 17.2 | 2.0 | 784 | 457 | 675 |
| 12 | 3.5 | 11.6 | 2.0 | 863 | 487 | 695 |
| 13 | 0 | 12.2 | 4.4 | 893 | 471 | 690 |

EXAMPLE 5

Case No 5: Female, 65 years old.

Diagnosis: Adenocarcinoma of the breast (ductal, infiltrating); widely metastasized.

Basis of diagnosis: Tumorectomy with histological analyses (on two separate occasions); X-rays; (lungs); liver scans; bone scans.

Therapy prior to present treatment: Surgery, extensive conventional (mitoxin) chemotherapy; radiation; anti-estrogen drugs.

Tumor status at start of present treatment: Widely disseminated metastases; protruding superficial tumor mass, hard, fixed, 3 cm. diameter just below left collarbone; protruding superficial tumor, hard, semimobile, in surgical scar (1 cm. diameter) on left breast; metastases in both lungs; multiple bone metastases: skull, spine, pelvis (extensive destruction), femurs; extensive liver metastases. Patient is in intense pain, primarily pelvic, spinal, and right lower jaw; pain intensifies with movement; pancytopenia; arthritis of many years duration; stomatitis; history of sporadic hypoglycemia; elevated urine estrogen; many emotional problems; vital signs normal. Unable to walk or even get out of bed because of pain.

Response to treatment:

| | | A. Phase I | |
|---|---|---|---|
| Day | Tumor Dimension | % Reduction in Tumor Mass | Doctor's Progress Notes |
| 1 | 3.0 (cb) (see progress note) 1.0 (br) (see progress | — | Patient starts with Dnr; no DNP. Patient suffers intense pain, especially upon movement; unable to get out |

-continued

| | A. Phase I | | |
|---|---|---|---|
| Day | Tumor Dimension | % Reduction in Tumor Mass | Doctor's Progress Notes |
| | note) | | of bed or walk. ("cb" denotes the superficially protruding tumor mass below the collarbone; "br" denotes the tumor mass in the surgical scar on the left breast). |
| 2 | — | — | Starts with DNP. Patient reports pain at all levels is less, although still appreciable. |
| 4 | — | — | Patient reports that pain at all levels is greatly diminished; is in much better spirits and more cooperative. |
| 5 | — | — | Patient reports that pain at all levels has essentially subsided; is walking about with aid of walker; is able to get out of bed by self; is in excellent spirits. |
| 8 | (see progress note) | (see progress note) | Patient remains practically free of pain; walks about easily with aid of walker; reports that she is sure tumors under the collarbone and in surgical scar are diminishing in size. |
| 10 | — | — | Patient reports slight back pain, but is fine otherwise; still moving about freely with aid of walker; Bmr = 1.44. |
| 11 | — | — | Patient reports perspiring appreciably last night; some shortness of breath; vital signs normal; Bmr = 1.73. |
| 12 | — | — | Final day of treatment period (Phase I); Bmr = 2.19; patient remains in bed. |
| 13 | 1.2 (cb) 0.4 (br) | 93.6 93.6 | Patient reports feeling tired, but otherwise OK; vital signs normal; oncologist reports dramatic shrinkage of observable tumors over the past 2-day period; residual tumor masses much softer; both only slightly protrusive. |

The oncologist noted the following: Throughout the treatment period the patient's body weight, blood pressure, pulse rate, respiratory rate, temperature, and blood cytological and chemical parameters remained stable and within the normal range. The DNP produced the intended transient increase in metabolic rate. No side-effects due to the DNP per se were observed. This patient had many family and emotional problems and was intensely unhappy with hospital confinement and regimentation of diet, being unaware of the seriousness of her condition; became most uncooperative and undependable in taking the required Dnr; was eventually released at her insistence. Despite this impediment and the extensive metastatic infiltration of the liver, she responded excellently to the treatment regimen; her body weight remained stable and her hemoglobin increased 16%. A bone scan performed on day 28 (15 days after the completion of the treatment period, and during which time she had been on a normal protein intake) revealed a significant improvement in the various bone metastases with several of the initial lesions having essentially disappeared. Her plasma calcium remained fully normal during her stay at the hospital despite the extensive bone metastases; however, she began to exhibit increasingly severe hypercalcemia within a short time after leaving and resuming her regular diet.

Table V below summarizes the daily treatment conditions with this patient:

TABLE V

| Case No. 5: Daily Treatment Conditions A. Phase I | | | | | | |
|---|---|---|---|---|---|---|
| Day (No.) | DNP (mg/kg) | Pr (g) | Efa (ml) | Cho (g) | Bmr ($lO_2/d$) | $Emr_A$ ($lO_2/d$) |
| 1 | 0 | 10.5 | 2.37 | 469 | not measured | 367 |
| 2 | 1.5 | 10.5 | 2.37 | 334 | 287 | 266 |
| 3 | 1.5 | 10.5 | 2.37 | 334 | 341 | 266 |
| 4 | 1.5 | 10.5 | 2.37 | 428 | 313 | 336 |
| 5 | 1.5 | 10.5 | 2.37 | 511 | 390 | 398 |
| 6 | 1.5 | 10.5 | 2.37 | 533 | 317 | 415 |
| 7 | 1.0 | 10.5 | 2.37 | 533 | 360 | 415 |
| 8 | 1.0 | 17.6 | 2.37 | 473 | 334 | 441 |
| 9 | 0 | 17.6 | 2.37 | 528 | 399 | 420 |
| 10 | 0 | 10.1 | 2.37 | 533 | 403 | 450 |
| 11 | 0 | 2.5 | 2.37 | 533 | 483 | 528 |
| 12 | 0 | 5.5 | 2.37 | 666 | 611 | 659 |

EXAMPLE 6

Case No. 6: Male, 64 years old.

Diagnosis: Carcinoma of the lung (large-cell, undifferentiated); upper lobe, right lung.

Basis of diagnosis: Histological analysis of tumor specimens (2 independent analyses); X-rays.

Therapy prior to present treatment: Laetrile; dietary.

Tumor status at start of present treatment: Tumor activity confined to upper lobe of right lung, which X-rays show to be completely opacified due to tumor and atelectasis; no metastases detectable elsewhere (liver, bone, lymph nodes, viscera). Patient is very thin and pale; anemic; suffers a 25% reduction in oxygenation capacity and occasional episodes of shortness of breath; has heart murmur with extrasystole; tires easily; has periodic episodes of coughing; appetite good; no pain; reasonably good general condition; vital signs normal.

Response to treatment:

| A. Phase I | | |
|---|---|---|
| Day | Indications of Tumor Status/Response | Doctor's Progress Notes |
| 1 | — | Patient starts on Dnr; no DNP. |
| 2 | — | Patient starts on DNP. |
| 6 | — | Patient in good condition; feels fatigued upon walking vital signs normal; appetite good. |
| 11 | — | Patient in excellent condition; much improved color in skin and mucosa; red blood cell count has in- |

A. Phase I (continued)

| Day | Indications of Tumor Status/Response | Doctor's Progress Notes |
|---|---|---|
| 12 | — | creased; Bmr rose to 1.93; no complaint of dyspnea. Final day of treatment period (Phase I). DNP has been discontinued; patient feeling fine; vital signs normal; Bmr = 2.70; patient walking about with no complaint of dyspnea. Patient feels fine; color improvement very noticeable vital signs normal. |
| 14 | Oncologists (2 independent examinations) report definite indications of increased ventilation of right lung; detect new sounds ascribed to ventilatory air flow. | Patient is in excellent condition. |
| 20 | Patient is able to take long walks without any occurrence of dyspnea; ventilation much improved in right lung. | Patient in excellent condition; reports a feeling of overall well-being. |

The oncologist noted the following: Throughout the treatment period the patient's body weight, blood pressure, pulse rate, respiratory rate, temperature, and blood cytological and chemical parameters remained stable and within the normal range, except for the initial anemia which greatly improved. The DNP produced the intended transient increase in metabolic rate; no side-effects due to the DNP per se were observed. The patient's hemoglobin increased 40% during his stay. The ventilation in his right lung continued to improve until departure. No specific identification of tumor masses per se could be made in any of the post-treatment X-rays, which revealed only the same uniform atelectatic opacity of the lobe as seen previously. Because of the significant functional improvement, and pressing family matters, the patient left for home before commencement of the Phase II treatment period.

The daily treatment conditions were as set forth in Table VI:

TABLE VI

Case No. 6: Daily Treatment Conditions
A. Phase I

| Day (No.) | DNP (mg/kg) | Pr (g) | Efa (ml) | Cho (g) | Bmr ($lO_2/d$) | $Emr_A$ ($lO_2/d$) |
|---|---|---|---|---|---|---|
| 1 | 0 | 14.0 | 3.69 | 707 | not measured | 552 |
| 2 | 1.5 | 14.0 | 3.69 | 522 | 365 | 413 |
| 3 | 1.5 | 14.0 | 3.69 | 522 | 427 | 413 |
| 4 | 1.0 | 14.0 | 3.69 | 617 | 523 | 484 |
| 5 | 1.5 | 14.0 | 3.69 | 719 | 432 | 561 |
| 6 | 1.5 | 14.0 | 3.69 | 731 | 513 | 570 |
| 7 | 1.0 | 14.0 | 3.69 | 731 | 592 | 570 |
| 8 | 0.3 | 23.4 | 3.69 | 802 | 612 | 741 |
| 9 | 0 | 23.4 | 3.69 | 890 | 625 | 700 |
| 10 | 0.3 | 15.9 | 3.69 | 849 | 585 | 695 |
| 11 | 0 | 6.0 | 3.69 | 849 | 705 | 748 |
| 12 | 0 | 9.0 | 3.7 | 889 | 984 | 986 |

EXAMPLE 7

Case No. 7: Male, 67 1 years old.

Diagnosis: Carcinoma of the lung (oat-cell, undifferentiated); tumor located in left hilum with extensive diffuse infiltration into surrounding lung tissue.

Basis of diagnosis: Bronchoscopy with biopsy (at junction of left upper and lower lobes); X-rays.

Therapy prior to present treatment: None.

Tumor status at start of present treatment: Tumor mass centered in the left hilum with extensive diffuse infiltration of surrounding tissue; no evidence of liver, bone, or brain metastases on respective scans; lymph node areas negative except for one suspicious 6 mm. node in the left base of the neck. Patient is very thin and losing weight rapidly because of nervous anorexia; is extremely nervous and under great emotional strain because of family pressures upon him; has frequent gastritis; has severe spells of violent coughing, which are increasing steadily in frequency and duration; suffers shortness of breath; occasional retrosternal pain; vital signs normal; blood parameters, liver function and urinalysis results normal.

Response to treatment:

A. Phase I

| Day | Indications of Tumor Status/Response | Doctor's Progress Notes |
|---|---|---|
| 1 | Patient has frequent and violent coughing spells; uses codeine cough syrup, but with little benefit; reports increased retrosternal pain and shortness of breath when excited or agitated. | Patient starts on Dnr; no DNP |
| 2 | — | Patient starts on DNP. |
| 6 | Patient reports coughing spell less violent. | Patient reports feeling of improvement and overall wellbeing, despite gastritis induced by emotional upset of family problems. |
| 7 | Patient reports coughing spells milder and less frequent | Bmr = 1.39 today; patient feels fine; no dyspnea. |
| 11 | Coughing episodes continue to decrease, in intensity, duration, and frequency. Patient experiences no dyspnea, despite elevated Bmr and active walking about. | Patient in good general condition despite continuing emotional upset due to family problems; vital signs normal; Bmr up to 2.03 today. |
| 12 | — | Final day of treatment period (Phase I); DNP discontinued yesterday; Bmr = 1.84 today. |
| 13 | Patient reports retrosternal pain has disappeared. | Vital signs all normal; patient feels fine physically. |
| 14 | Patient reports coughing episodes are now minimal. | Vital signs all normal; blood parameters normal, including serum total protein level. |
| 15 | Patient reports coughing has completely stopped; retrosternal pain is gone; no shortness of breath even with active walking; blood urea nitrogen level has decreased relative to pretreatment level. | Patient reports feel of well being and great improvement; appetite has increased. |

The oncologist noted the following: Throughout the treatment the patient's body weight, blood pressure, pulse rate, respiratory rate, temperature, and blood cytological and chemical parameters remained stable and within the normal range. The DNP produced the intended transient increase in metabolic rate. No side-effects due to the DNP per se were observed. The patient left the hospital soon after completion of the Phase I treatment period because of continuing family problems, and did not receive the Phase II treatment.

Daily treatment conditions were as set forth in Table VII:

TABLE VII

Case No. 7: Daily Treatment Conditions
A. Phase I

| Day (No.) | DNP (mg/kg) | Pr (g) | Efa (ml) | Cho (g) | Bmr (lO$_2$/d) | Emr$_A$ (lO$_2$/d) |
|---|---|---|---|---|---|---|
| 1 | 0 | 13.6 | 3.6 | 690 | not measured | 538 |
| 2 | 1.5 | 13.6 | 3.6 | 507 | 340 | 401 |
| 3 | 1.5 | 13.6 | 3.6 | 507 | 353 | 401 |
| 4 | 1.0 | 13.6 | 3.6 | 606 | 445 | 475 |
| 5 | 1.5 | 13.6 | 3.6 | 747 | 445 | 581 |
| 6 | 1.5 | 13.6 | 3.6 | 772 | 373 | 600 |
| 7 | 1.5 | 13.6 | 3.6 | 706 | 474 | 550 |
| 8 | 1.5 | 22.5 | 3.6 | 577 | 439 | 540 |
| 9 | 0 | 22.5 | 3.6 | 678 | 532 | 540 |
| 10 | 1.0 | 18.9 | 3.6 | 672 | 444 | 541 |
| 11 | 0 | 5.6 | 3.6 | 672 | 692 | 670 |
| 12 | 0 | 8.5 | 3.6 | 672 | 627 | 670 |

EXAMPLE 8

Case No. 8: Female, 57 years old.

Diagnosis: Adenocarcinoma (poorly differentiated; surgically unidentified primarily because of far advanced visceral spread); (clinically colon); numerous liver and other metastases.

Basis of diagnosis: Laparotomy with multiple biopsies; X-rays; scans.

Therapy prior to present treatment: Extensive semi-continuous conventional (mitoxin) chemotherapy over a prolonged period.

Tumor status at start of present therapy: Extensive metastatic tumor activity throughout body: brain, bones, viscera, liver (extensive metastases), both lungs, lymph nodes. Patient is in late terminal state; in intense general pain (headache, right chest, rib cage, abdomen, spine) even though under heavy sedation; has hypercalcemia; cannot maintain balance or walk; nausea; very weak; anorexic. (Note: Although this patient was clinically considered to be fully terminal, it was decided to attempt to administer the Phase I treatment to the extent that the Dnr intake could continue to be reasonably maintained).

Response to treatment:

A. Phase I

| Day | Indication of Tumor Status/Response | Doctor's Progress Notes |
|---|---|---|
| 1 | — | Patient starts on Dnr; no DNP. Patient is in intense pain especially headache; very restless; semiconfused; confined to bed; vital signs normal; blood parameters normal except moderate hypercalcemia. |
| 2 | Headache has decreased in intensity | Patient taking Dnr on schedule; no DNP; still feels very weak. |
| 3 | Headache and other pain has diminished greatly; pain medication has been reduced to very low level. | Patient is much improved; more alert and communicative; no DNP given yet. |
| 4 | Pain continues to diminish at all sites. | Patient in stable state; more cooperative; continues on Dnr; starts on DNP (first dose). |
| 5 | Headache and other pains are essentially gone. | Patient deemed to be improved sufficiently by oncologist to commence with daily palliative radiation treatments of large brain-metastasis tomorrow; serum calcium has increased 11%. |
| 7 | Pain has disappeared at all sites; all pain medicine is stopped. | Patient is less restless; slept well; vital signs all normal. Patient received first radiation treatment at noon; was drowsy and semiconfused all afternoon. |
| 9 | Patient remains pain-free. Patient has become free of any clinical signs of hypercalcemia. | Patient reports feeling much better in morning before radiation treatments; becomes tired, drowsy, confused, and uncooperative after radiation treatments. |
| 10 | Patient remains free of pain at all sites. | Patient better oriented; much less confused; more cooperative; vital signs normal; Bmr has started increasing (1.26). No radiation treatment today. |
| 11 | Patient continues free of pain. | Final day of treatment period (Phase I); DNP discontinued yesterday. Patient greatly improved; is able to carry on coherent conversation with visitors; vital signs normal; Bmr has elevated to 1.99; no radiation today. |
| 12 | No pain whatever. | Patient is very alert and cooperative prior to radiation treatment; reports feel- |

-continued

A. Phase I

| Day | Indication of Tumor Status/Response | Doctor's Progress Notes |
|---|---|---|
| 13 | No pain at any level; no signs of hypercalcemia. | ing very tired after radiation treatment sleeps most of the afternoon; irritable. Patient requests discontinuance of daily radiation treatments; as she feels much better before treatment and very bad after it; continues to improve generally. |

The oncologist noted the following: Throughout the treatment period the patient's body weight, blood pressure, pulse rate, respiratory rate, temperature, and blood cytological and chemical parameters remained stable and within the normal range, except for the increasing initial hypercalcemia she had at time of entry. The DNP produced the intended transient increase in metabolic rate; no side-effects attributable to DNP per se were observed. The patient was continued on daily radiation treatments by the oncologist for another week after her request that they be stopped. Just prior to the last radiation treatment (day 19) the patient slipped in the bathroom at night and suffered an orbital hematoma, with apparent additional internal bleeding of undetermined origin, and eventually became comatose therefrom (day 24). However, she responded rapidly to an infusion of whole blood and improved somewhat, but remained in a state of general malaise and unsteadiness. The hypercalcemic state elevated rapidly during this period, when she was only minimally on the Dnr. She was released (day 27) at the request of her family and did not participate in the Phase II treatment period.

Table VIII summarizes the daily treatment conditions for this patient:

TABLE VIII

Case No. 8: Daily Treatment Conditions
A. Phase I

| Day (No.) | DNP (mg/kg) | Pr (g) | Efa (ml) | Cho (g) | Bmr (lO$_2$/d) | Emr$_A$ (lO$_2$/d) |
|---|---|---|---|---|---|---|
| 1 | 0 | 11.8 | 2.9 | 407 | not measured | 323 |
| 2 | 0 | 11.8 | 2.9 | 407 | 329 | 323 |
| 3 | 0 | 11.8 | 2.9 | 407 | 293 | 323 |
| 4 | 1.5 | 11.8 | 2.9 | 446 | 308 | 352 |
| 5 | 2.0 | 11.8 | 2.9 | 457 | 344 | 360 |
| 6 | 1.0 | 11.8 | 2.9 | 510 | not measured | 400 |
| 7 | 1.0 | 19.6 | 2.9 | 480 | 349 | 450 |
| 8 | 0 | 19.6 | 2.9 | 512 | 336 | 411 |
| 9 | 1.5 | 12.0 | 2.9 | 409 | 414 | 360 |
| 10 | 0 | 3.7 | 2.9 | 409 | not measured | 439 |
| 11 | 0 | 6.7 | 2.9 | 409 | 255 | 411 |
| 12 | 0 | 23.2 | 2.9 | 521 | not measured | 420 |

While the invention has been described in connection with specific embodiments thereof, it will be understood that it is capable of further modification and that this application is intended to cover any variations, uses, or adaptations of the invention following, in general, the principles of the invention and including such departures from the present disclosure as come within the ordinary skill of the art to which the invention pertains, and as may be applied to the essential features hereinbefore set forth, within the spirit of the invention and the scope of the appended claims.

What is claimed is:

1. A method for effecting oncolysis in a mammal with a malignant condition characterized by an in vivo metabolism in the cells wherein said cells are substantially unable to utilize glucose for the production of adenosine triphosphate (ATP), which method comprises elevating said mammal's basal metabolic rate as far as therapeutically tolerable by administering a combination of
   (a) a predetermined periodic dosage of physiologically tolerable agent capable of uncoupling oxidative phosphorylation in said mammal, and
   (b) a daily nutritional regimen selected with reference to the basal and active metabolic rates of said mammal so as to provide only a minimum daily caloric requirement for said mammal, which is allocated among,
      (i) an amount of amino acids just sufficient to maintain minimal bodily nitrogen balance,
      (ii) a minimum amount of essential fatty acids, and
      (iii) the balance in the form of glucose or physiological precursors thereof.

2. The method of claim 1 in which said periodic dosage of said agent and said daily nutritional metabolite regimen are reevaluated and adjusted in accordance with measured changes in said mammal's basal and active metabolic rates.

3. The method of claim 1 wherein the uncoupling agent is selected from among 2,4-dinitrophenol, 2,6-dinitrophenol, 4,6-dinitrocresol and mixtures of any of them.

4. A method according to any of claims 1, 2 or 3 wherein either or both of the minimum daily caloric requirement and the uncoupling agent may be administered orally or parenterally.

5. A method according to claim 4 wherein the minimum daily caloric requirement, expressed as kilocalories per day, is measured at about one-half the sum of said mammal's basal and active metabolic rates, each expressed in kilocalories per day.

6. A method according to claim 4 wherein said amount of amino acids provides daily nitrogen intake for said mammal substantially equal to the minimum total daily nitrogen execreted in urine by said mammal and said minimum amount of fatty acids corresponds to about 1% of said minimum daily caloric requirement at the commencement of administration of the method.

7. A method according to claim 4 wherein said mammal is a human being.

8. A method according to any of claims 1, 2 or 3 wherein the minimum daily caloric requirement, expressed as kilocalories per day is measured at about one-half the sum of said mammal's basal and active metabolic rates, each expressed in kilocalories per day.

9. A method according to claim 8 wherein said amount of amino acids provides daily nitrogen intake for said mammal substantially equal to the minimum total daily nitrogen execreted in urine by said mammal and said minimum amount of fatty acids corresponds to about 1% of said minimum daily caloric requirement at the commencement of adminstration of the method.

10. A method according to claim 8 wherein said mammal is a human being.

11. A method according to any of claims 1, 2 or 3 wherein said amount of amino acids provides daily nitrogen intake for said mammal substantially equal to the minimum total daily nitrogen execreted in urine by said mammal and said minimum amount of fatty acids corresponds to about 1% of said minimum daily caloric requirement at the commencement of adminstration of the method as described in claim 1.

12. A method according to claim 11 wherein said mammal is a human being.

13. A method according to any of claims 1, 2 or 3 wherein said mammal is a human being.

14. A method according to claim 13 wherein said human being's basal metabolic rate is elevated to a level between about 1.3 and 3.0 times the Mayo Normal Standard basal metabolic rate for said human being.

15. A method according to claim 13 wherein said amount of amino acids supplies from about 5 to about 15 grams of protein per day per 70 grams of body weight of said human being.

Figure 1:
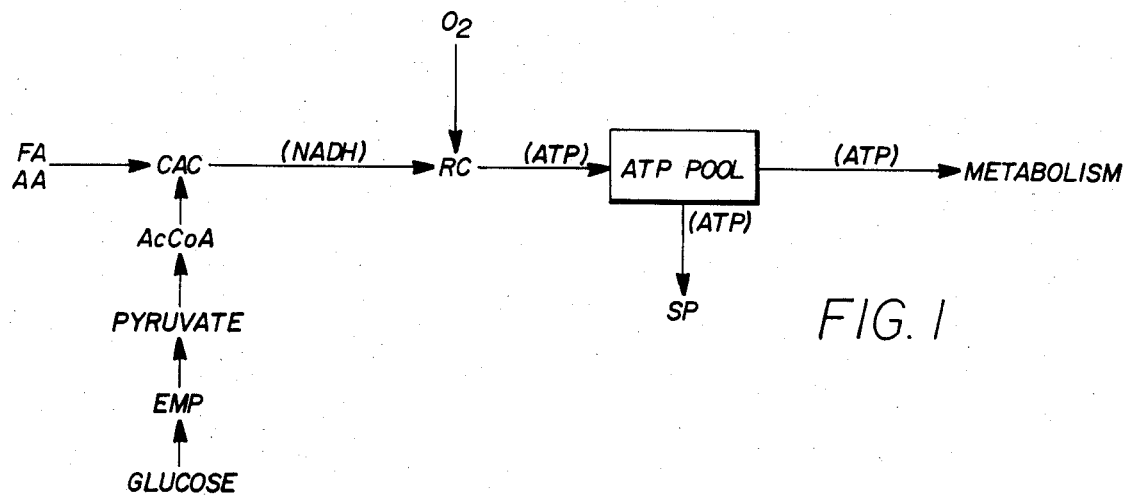
FIG. 1 is a flow diagram depicting the energy pathway for ATP production and usage in normal cells.
Figure 2:
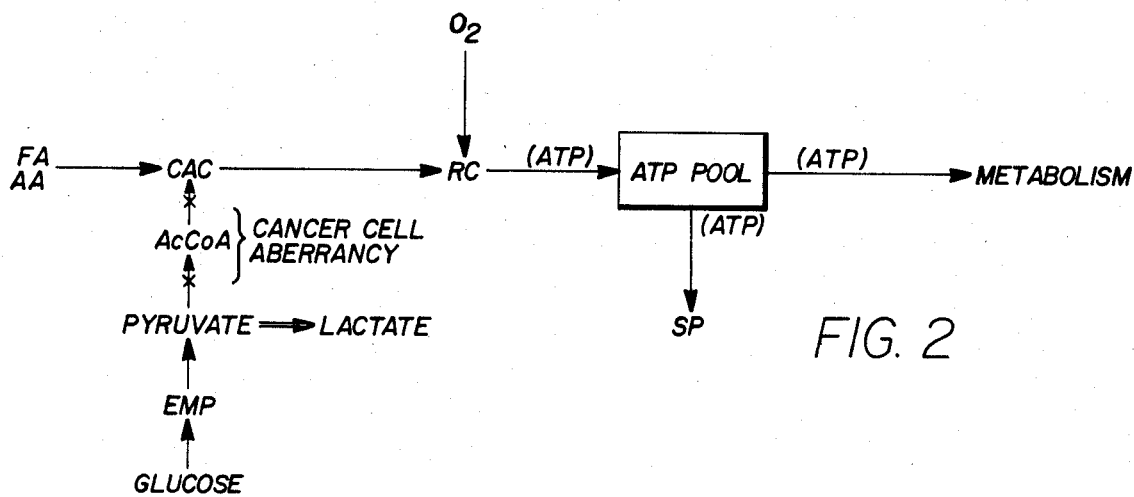
FIG. 2 is a flow diagram depicting the energy pathway for ATP production and usage in malignant cells. The (→→) means a substantially reduced rate of flow, whereas (⇒) means a substantially increased rate of flow.

16. A method of selectively decreasing the rate of ATP production in malignant cells of a mammal without substantially altering the rate of ATP production in the normal cells of said mammal, wherein the malignant cells undergo in vivo metabolism according to the metabolic pathway depicted in FIG. 2 hereof, which method comprises elevating said mammal's basal metabolic rate as far as therapeutically tolerable by administering a combination of
   (a) a predetermined periodic dosage of physiologically tolerable agent capable of uncoupling oxidative phosphorylation in said mammal, and
   (b) a daily nutritional regimen selected with reference to the basal and active metabolic rates of said mammal so as to provide only a minimum daily caloric requirement for said mammal, which is allocated among,
      (i) an amount of amino acids just sufficient to maintain minimal bodily nitrogen balance,
      (ii) a minimum amount of essential fatty acids, and
      (iii) the balance in the form of glucose or physiological precorsors thereof.

17. The method of claim 16 in which said periodic dosage of said agent and said daily nutritional regimen are reevaluated and adjusted, in accordance with measured changes in said mammal's basal and active metabolic rates.

18. The method of claim 16 wherein the uncoupling agent is selected from among 2,4-dinitrophenol, 2,6-dinitrophenol, 4,6-dinitrocresol and mixtures of any of them.

19. A method according to any of claims 16, 17 or 18 wherein either or both of the minimum daily caloric requirement and the uncoupling agent may be administered orally or parenterally.

20. A method according to claim 19 wherein the minimum daily caloric requirement, expressed as kilocalories per day, is measured at about one-half the sum of said mammal's basal and active metabolic rates, each expressed in kilocallories per day.

21. A method according to claim 19 wherein said amount of amino acids provides daily nitrogen intake for said mammal substantially equal to the minimum total daily nitrogen excreted in urine by said mammal and said minimum amount of fatty acids corresponds to about 1% of said minimum daily caloric requirement at the commencement of administration of the method.

22. A method according to claim 19 wherein said mammal is a human being.

23. A method according to any of claims 16, 17 or 18 wherein the minimum daily caloric requirement, expressed as kilocalories per day, is measured at about one-half the sum of said mammal's basal and active metabolic rates, each expressed in kilocalories per day.

24. A method according to claim 23 wherein said amount of amino acids provides daily nitrogen intake for said mammal substantially equal to the minimum total daily nitrogen execreted in urine by said mammal and said minimum amount of fatty acids corresponds to about 1% of said minimum daily caloric requirement at the commencement of administration of the method.

25. A method according to any of claims 16, 17 or 18 wherein said amount of amino acids provides daily nitrogen intake for said mammal substantially equal to the minimum total daily nitrogen excreted in urine by said mammal and said minimum amount of fatty acids corresponds to about 1% of said minimum daily caloric requirement at the commencement of adminstration of the method as described in claim 16.

26. A method according to claim 23 wherein said mammal is a human being.

27. A method according to claim 25 wherein said mammal is a human being.

28. A method according to any of claims 16, 17 or 18 wherein said mammal is a human being.

29. A method according to claim 28 wherein said human being's basal metabolic rate is elevated to a level between about 1.3 and 3.0 times the Mayo Normal Standard basal metabolic rate for said human being.

30. A method according to claim 28 wherein said amount of amino acids supplies from about 5 to about 15 grams of protein per day per 70 grams of body weight of said human being.

* * * * *

UNITED STATES PATENT AND TRADEMARK OFFICE
CERTIFICATE OF CORRECTION

PATENT NO. : 4,724,234

DATED : February 9, 1988

INVENTOR(S) : Clarence D. Cone, Jr.

It is certified that error appears in the above-identified patent and that said Letters Patent is hereby corrected as shown below:

Col 1, line 49, add "chlorine" after "$Cl^-$" so that it reads "$Cl^-$ chlorine ion"

Col 5, line 23, add "59," before "419 (1937)" so that it reads "59, 419(1937)"

Col 8, line 61, add "i" after "per" and before "cellular" so that it reads "pericellular"

Col 10, line 32, add a hyphen to "normalcell" so that it reads "normal-cell"

Col 13, line 64, add a hyphen to "glucoseutilization" so that it reads "glucose-utilization"

Col 14, line 56, add a period after "phases" and before "Phase I" so that it reads "phases.  Phase I"

Col 17, line 35, add "r" after "P" so that it reads "$Pr=Pr_{min}$"

Col 18, line 63, add "ro" after "3,4,5-trichlo" so that it reads "3,4',5-trichloronitrosalicylanilide"

Col 19, lines 31-32 add "a very great" before "number of," delete "a very great" after "number of" so that it reads "a very great number of laboratory studies"

Col 20, line 8, add "by" after "produced" and before "$D_A$" so that it reads "produced by $D_A$"

UNITED STATES PATENT AND TRADEMARK OFFICE
CERTIFICATE OF CORRECTION

PATENT NO. : 4,724,234
DATED : February 9, 1988
INVENTOR(S) : Clarence D. Cone, Jr.

It is certified that error appears in the above-identified patent and that said Letters Patent is hereby corrected as shown below:

Col 20, line 27 "Phse I" should read "Phase I"

Col 22, lines 19,24 "tumour" should read "tumor"

Col 26, line 60 "resipratory" should read "respiratory"

Col 26, line 65 "dirctly" should read "directly"

Col 27, line 53 "noraml" should read "normal"

Col 33, line 24, add "s" after "feel" so that it reads "feels fine"

Col 38, line 3, delete "1" after '67" so that it reads "67 years old"

Col 44, line 9, "kilocallories" should read "kilocalories"

Signed and Sealed this

Thirteenth Day of September, 1988

Attest:

DONALD J. QUIGG

Attesting Officer      Commissioner of Patents and Trademarks